United States Patent
Yildiz et al.

(10) Patent No.: US 10,591,737 B2
(45) Date of Patent: Mar. 17, 2020

(54) SYSTEMS AND METHODS FOR AUTOMATIC ADJUSTMENT OF HEAD MOUNTED DISPLAY STRAPS

(71) Applicant: Dell Products L.P., Round Rock, TX (US)

(72) Inventors: Yagiz Can Yildiz, Austin, TX (US); Christopher A. Torres, San Marcos, TX (US)

(73) Assignee: Dell Products L.P., Round Rock, TX (US)

( * ) Notice: Subject to any disclaimer, the term of this patent is extended or adjusted under 35 U.S.C. 154(b) by 48 days.

(21) Appl. No.: 15/958,907

(22) Filed: Apr. 20, 2018

(65) Prior Publication Data

US 2019/0324280 A1    Oct. 24, 2019

(51) Int. Cl.
| | |
|---|---|
| *G02B 27/01* | (2006.01) |
| *G06F 3/01* | (2006.01) |
| *A61B 5/00* | (2006.01) |
| *A44B 11/20* | (2006.01) |

(52) U.S. Cl.
CPC .......... *G02B 27/0176* (2013.01); *A44B 11/20* (2013.01); *A61B 5/6803* (2013.01); *A61B 5/6831* (2013.01); *G02B 27/0172* (2013.01); *G06F 3/013* (2013.01)

(58) Field of Classification Search
CPC . G02B 27/0176; G02B 27/0172; A44B 11/20; A61B 5/6803; A61B 5/6831; G06F 3/013
See application file for complete search history.

(56) References Cited

U.S. PATENT DOCUMENTS

| | | | | |
|---|---|---|---|---|
| 4,852,988 | A  * | 8/1989 | Velez ..................... | A61B 3/113 351/210 |
| 2013/0234915 | A1* | 9/2013 | Takeda ............... | G02B 27/0172 345/8 |
| 2014/0375540 | A1* | 12/2014 | Ackerman .............. | G06F 3/013 345/156 |
| 2018/0032133 | A1* | 2/2018 | Cho ........................ | G06F 3/013 |
| 2018/0046147 | A1* | 2/2018 | Aghara ................ | A61B 5/1172 |

* cited by examiner

*Primary Examiner* — Afroza Chowdhury
(74) *Attorney, Agent, or Firm* — Baker Botts L.L.P.

(57) ABSTRACT

Systems and methods are disclosed for automatic adjustment of straps of a head mounted display. The head mounted display may include a display device, a plurality of straps, and a controller. The controller may monitor eye location data of at least one eye of a user using at least one eye tracking sensor. The controller may direct the user to move the display device to achieve a desired image being displayed on the display device based on the monitored eye location data and accepted eye location data. The controller may monitor strap pressure data associated with the plurality of straps using a plurality of the pressure sensors. The controller may adjust each strap of the plurality of straps using an adjustment actuator to achieve a desired fit of the head mounted display on the user based on the monitored strap pressure data and accepted strap pressure data.

20 Claims, 11 Drawing Sheets

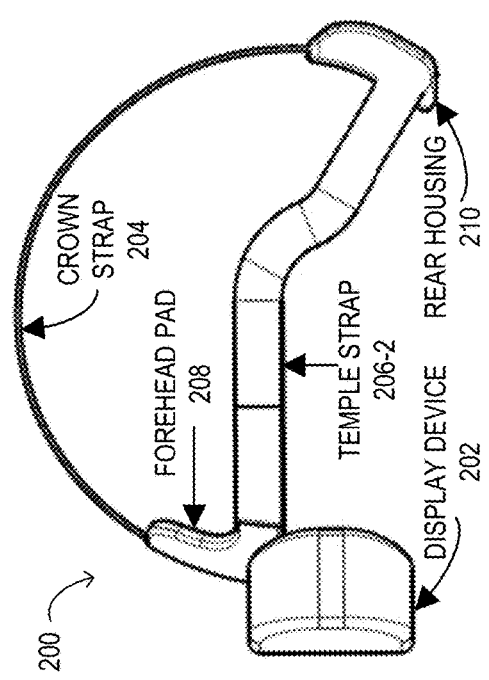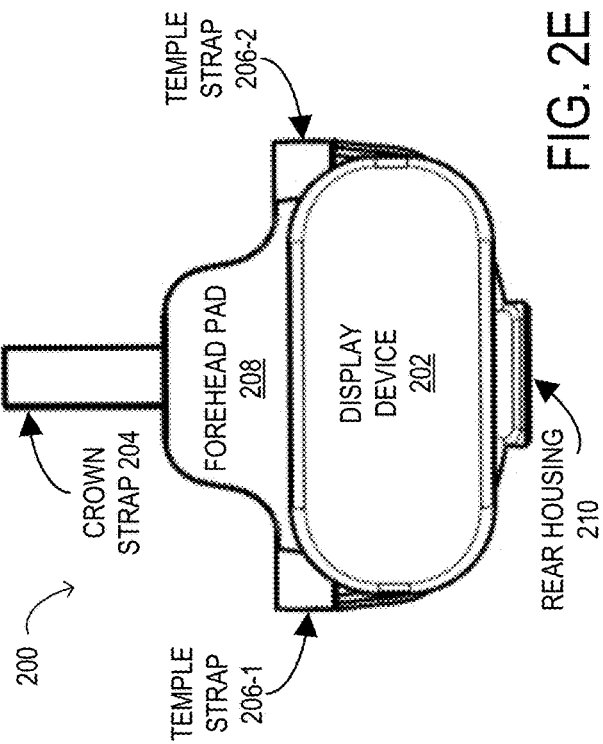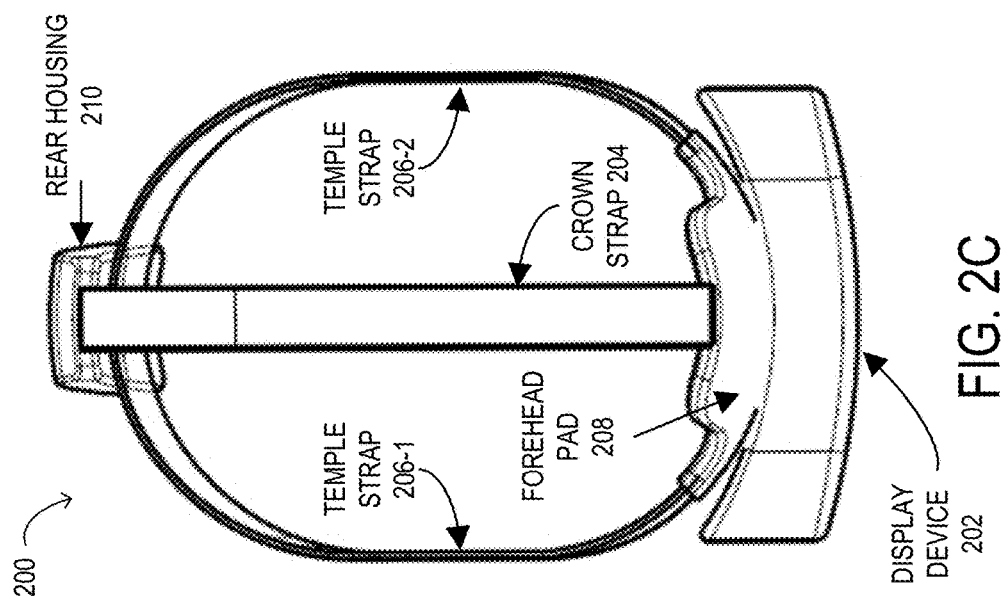

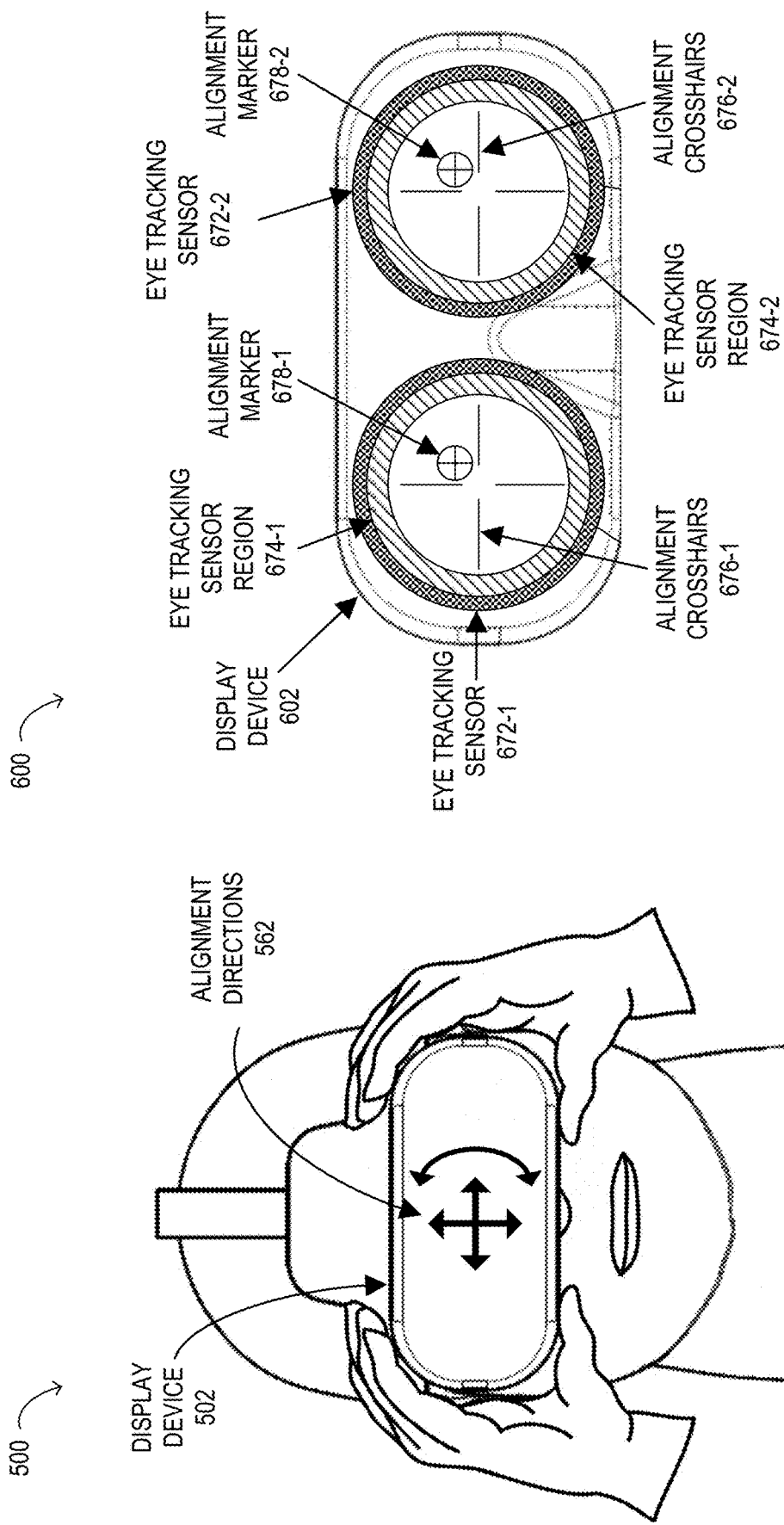

SYSTEMS AND METHODS FOR AUTOMATIC ADJUSTMENT OF HEAD MOUNTED DISPLAY STRAPS

BACKGROUND

Field of the Disclosure

This disclosure relates generally to information handling systems and, more particularly, to systems and methods for automatic adjustment of head mounted display straps.

Description of the Related Art

As the value and use of information continues to increase, individuals and businesses seek additional ways to process and store information. One option available to users is information handling systems. An information handling system generally processes, compiles, stores, and/or communicates information or data for business, personal, or other purposes thereby allowing users to take advantage of the value of the information. Because technology and information handling needs and requirements vary between different users or applications, information handling systems may also vary regarding what information is handled, how the information is handled, how much information is processed, stored, or communicated, and how quickly and efficiently the information may be processed, stored, or communicated. The variations in information handling systems allow for information handling systems to be general or configured for a specific user or specific use such as financial transaction processing, airline reservations, enterprise data storage, or global communications. In addition, information handling systems may include a variety of hardware and software components that may be configured to process, store, and communicate information and may include one or more computer systems, data storage systems, and networking systems.

Examples of information handling systems include display devices, head mounted display devices, head mount display systems, desktop computers, server systems, microprocessors, controllers, microcontroller units, and/or combinations thereof.

SUMMARY

In one embodiment, a disclosed head mounted display may include a display device, at least one eye tracking sensor disposed in the display device, a plurality of straps coupled to the display device, a plurality of pressure sensors associated with the plurality of straps, at least one adjustment actuator coupled to the plurality of straps, and a controller. The controller may identify user fit information associated with a user of the head mounted display. The user fit information may describe accepted eye location data, accepted strap pressure data, and accepted strap position data of each strap of the head mounted display on the user. The controller may also monitor eye location data of the at least one eye using the at least one eye tracking sensor. The controller may further, when the user fit information associated with the user has been identified, direct the user to move the display device that may achieve a desired image being displayed on the display device based on the monitored eye location data and the accepted eye location data of the user fit information. The controller may also monitor strap pressure data associated with the plurality of straps using the plurality of the pressure sensors. The controller may further adjust a position of each strap of the plurality of straps using the at least one adjustment actuator that may achieve a desired fit of the head mounted display on the user based on the monitored strap pressure data, the accepted strap pressure data of the user fit information, and the accepted strap position data of each strap of the user fit information.

In a number of the disclosed embodiments of the head mounted display, the controller may further, when the controller failed to identify the user fit information associated with the user, direct the user to move the display device that achieve the desired image being displayed on the display device based on the monitored eye location data. The controller may also monitor strap pressure data associated with the plurality of straps using the plurality of the pressure sensors. The controller may further adjust the position of each strap of the plurality of straps using the at least one adjustment actuator that may achieve an accepted fit of the head mounted display on the user based on the monitored strap pressure data. The controller may also record the monitored eye location data, the monitored strap pressure data, and the adjusted strap position data of each strap at the accepted eye location data, the accepted strap pressure data, and the accepted strap position data of each strap respectively of the user fit information associated with the user.

In a number of the disclosed embodiments of the head mounted display, the plurality of straps may include a crown strap that may include a first end and a second end. The second end of the crown strap may be coupled to the display device proximate a top center portion of the display device. The plurality of straps may also include a first temple strap that may include a first end and a second end. The first end of the first temple strap may be coupled to the display device proximate a first side portion of the display device. The plurality of straps may further include a second temple strap that may include a first end and a second end. The first end of the second temple strap may be coupled to the display device proximate a second side portion of the display device opposite the first side portion of the display device, and the second end of the second temple strap may be coupled to the second end of the crown temple strap and the second end of the first temple strap.

In a number of the disclosed embodiments of the head mounted display, the desired image being displayed on the display device may include an alignment crosshair and an alignment marker associated with a respective eye of the at least one eye of the user. The desired image may be achieved when the user moved the display device such that the alignment marker is aligned with the alignment crosshair associated with the respective eye.

In a number of the disclosed embodiments of the head mounted display, the head mounted display may further include a plurality of strap position sensors, each of the plurality of strap position sensors may be associated with a respective strap of the plurality of straps. The controller may further monitor strap position data of each respective strap of the plurality of straps using each of the plurality of strap position sensors. The adjustment of the position of each respective strap of the plurality of straps may be further based on the strap position data of each respective strap of the plurality of straps.

In a number of the disclosed embodiments of the head mounted display, the controller may further monitor context information associated with the head mounted display. The controller may also, when the monitored context information may indicate that the accepted fit of the head mounted display on the user is to be changed, adjust the position of each strap of the plurality of straps using the at least one adjustment actuator that may achieve an updated fit of the head mounted display based on the monitored strap pressure data and the monitored context information. The updated fit may be within an operational range of the head mounted display that is greater than or equal to a loose fit threshold and less than or equal to a tight fit threshold.

In a number of the disclosed embodiments of the head mounted display, the monitored context information that may indicate that the accepted fit of the head mounted display on the user is to be changed that may be based on one or more of a motion sensor of the head mounted display may detect that movement of the head mounted display has exceeded a high movement change threshold, the motion sensor may detect that movement of the head mounted display has decreased below a low movement change threshold, an activity indicator may be received that indicates that that movement of the head mounted display is to exceed the high movement change threshold, the motion sensor may indicate that movement of the head mounted display is to decrease below the low movement change threshold, and the monitored strap pressure data may indicate that the desired fit of the head mounted display on the user has changed such that the desired fit is outside the operational range of the head mounted display.

In a number of the disclosed embodiments of the head mounted display, the controller may further, prior to identification of the user fit information associated with the user of the head mounted display, authenticate the user using an authentication process and one or more authentication devices coupled to the head mounted display. The authentication process may comprise one or more of IRIS recognition, facial recognition, finger recognition, retina recognition, voice recognition, and username and password verification. The identification of the user fit information associated with the user of the head mounted display may be based on the authentication process.

In a number of the disclosed embodiments of the head mounted display, the adjustment of the position of each strap of the plurality of straps using the at least one adjustment actuator may be further based on input from the user including at least one of a hand gesture by the user, a head gesture by the user, a voice command by the user, and adjustment input provided by an adjustment input device of the head mounted display initiated by the user.

In a number of the disclosed embodiments of the head mounted display, the at least one adjustment actuator may include a drive pinion, a drive stepper motor coupled to the drive pinion, and a drive rack coupled to the drive pinion. The drive rack may be disposed in at least one strap of the plurality of straps. The at least one adjustment actuator may, when the position of each strap is to be adjusted to increase the pressure of each strap that may achieve the accepted fit of the head mounted display, rotate, using the drive stepper motor, the drive pinion in a first rotational direction that may cause the drive pinion to move in a first direction along the drive rack to tighten each strap. The at least one adjustment actuator may also, when the position of each strap is to be adjusted to decrease the pressure of each strap that may achieve the accepted fit of the head mounted display, rotate, using the drive stepper motor, the drive pinion in a second rotational direction that may cause the drive pinion to move in a second direction along the drive rack to loosen each strap. The second rotational direction may be opposite the first rotational direction and the second direction may be opposite the first direction.

In a second embodiment, a disclosed method may include identifying, by a controller of a head mounted display, user fit information associated with a user of the head mounted display on the user. The user fit information may describe accepted eye location data of at least one eye of the user, accepted strap pressure data associated with a plurality of straps coupled to a display device of the head mounted display, and accepted strap position data of each strap of a plurality of straps. The method may also include monitoring eye location data of the at least one eye using at least one eye tracking sensor disposed in the display device. The method may further include, when the user fit information associated with the user has been identified, directing the user to move the display device that may achieve a desired image being displayed on the display device based on the monitored eye location data and the accepted eye location data of the user fit information, monitoring strap pressure data associated with the plurality of straps using a plurality of the pressure sensors associated with the plurality of straps, and adjusting a position of each strap of the plurality of straps using at least one adjustment actuator coupled to the plurality of straps that may achieve a desired fit of the head mounted display on the user based on the monitored strap pressure data, the accepted strap pressure data of the user fit information, and the accepted strap position data of each strap of the user fit information.

In a number of the disclosed embodiments of the method, the method may also include when the identification of the user fit information associated with the user may have failed, directing the user to move the display device that may achieve the desired image being displayed on the display device based on the monitored eye location data, monitoring strap pressure data associated with the plurality of straps using the plurality of the pressure sensors, adjusting the position of each strap of the plurality of straps using the at least one adjustment actuator that may achieve an accepted fit of the head mounted display on the user based on the monitored strap pressure data, and recording the monitored eye location data, the monitored strap pressure data, and the adjusted strap position data of each strap at the accepted eye location data, the accepted strap pressure data, and the accepted strap position data of each strap respectively of the user fit information associated with the user.

In a number of the disclosed embodiments of the method, the plurality of straps may include a crown strap that may include a first end and a second end. The second end of the crown strap may be coupled to the display device proximate a top center portion of the display device. The plurality of straps may also include a first temple strap that may include a first end and a second end. The first end of the first temple strap may be coupled to the display device proximate a first side portion of the display device. The plurality of straps may further include a second temple strap that may include a first end and a second end. The first end of the second temple strap may be coupled to the display device proximate a second side portion of the display device opposite the first side portion of the display device, and the second end of the second temple strap may be coupled to the second end of the crown temple strap and the second end of the first temple strap.

In a number of the disclosed embodiments of the method, the desired image being displayed on the display device may include an alignment crosshair and an alignment marker associated with a respective eye of the at least one eye of the user. The desired image may be achieved when the user moved the display device such that the alignment marker is aligned with the alignment crosshair associated with the respective eye.

In a number of the disclosed embodiments of the method, the method may also include monitoring strap position data of each respective strap of the plurality of straps using each of a plurality of strap position sensors of the head mounted display. Each of the plurality of strap position sensors may be associated with a respective strap of the plurality of straps. Adjusting the position of each respective strap of the plurality of straps may be further based on the strap position data of each respective strap of the plurality of straps.

In a number of the disclosed embodiments of the method, the method may also include monitoring context information associated with the head mounted display. The method may further include, when the monitored context information may indicate that the accepted fit of the head mounted display on the user is to be changed, adjusting the position of each strap of the plurality of straps using the at least one adjustment actuator that may achieve an updated fit of the head mounted display based on the monitored strap pressure data and the monitored context information. The updated fit may be within an operational range of the head mounted display that is greater than or equal to a loose fit threshold and less than or equal to a tight fit threshold.

In a number of the disclosed embodiments of the method, the monitored context information that may indicate that the accepted fit of the head mounted display on the user is to be changed that may be based on one or more of a motion sensor of the head mounted display may detect that movement of the head mounted display has exceeded a high movement change threshold, the motion sensor may detect that movement of the head mounted display has decreased below a low movement change threshold, an activity indicator may be received that indicates that that movement of the head mounted display is to exceed the high movement change threshold, the motion sensor may indicate that movement of the head mounted display is to decrease below the low movement change threshold, and the monitored strap pressure data may indicate that the desired fit of the head mounted display on the user has changed such that the desired fit is outside the operational range of the head mounted display.

In a number of the disclosed embodiments of the method, the method may further include, prior to identification of the user fit information associated with the user of the head mounted display, authenticating the user using an authentication process and one or more authentication devices that may be coupled to the head mounted display. The authentication process may comprise one or more of IRIS recognition, facial recognition, finger recognition, retina recognition, voice recognition, and username and password verification. The identification of the user fit information associated with the user of the head mounted display may be based on the authentication process.

In a number of the disclosed embodiments of the method, the adjustment of the position of each strap of the plurality of straps using the at least one adjustment actuator may be further based on input from the user that may include at least one of a hand gesture by the user, a head gesture by the user, a voice command by the user, and adjustment input provided by an adjustment input device of the head mounted display initiated by the user.

In a number of the disclosed embodiments of the method, the method may also include, when the position of each strap is to be adjusted to increase the pressure of each strap that may achieve the accepted fit of the head mounted display, rotating, by a drive stepper motor of the at least one adjustment actuator, a drive pinion of the at least one adjustment actuator in a first rotational direction that may cause the drive pinion to move in a first direction along a drive rack of the at least one adjustment actuator tightening each strap. The method may also include, when the position of each strap is to be adjusted to decrease the pressure of each strap that may achieve the accepted fit of the head mounted display, rotating, by the drive stepper motor, the drive pinion in a second rotational direction that may cause the drive pinion to move in a second direction along the drive rack loosening each strap. The second rotational direction may be opposite the first rotational direction and the second direction may be opposite the first direction.

BRIEF DESCRIPTION OF THE DRAWINGS

For a more complete understanding of the present invention and its features and advantages, reference is now made to the following description, taken in conjunction with the accompanying drawings, in which:

FIGS. 2A, 2B, 2C, 2D, and 2E are various views of selected elements of an embodiment of a head mounted display;

FIG. 5 is a front view of selected elements of an embodiment of a head mounted display;

FIG. 6 is a rear view of selected elements of an embodiment of a display device of a head mounted display;

Figure 1:
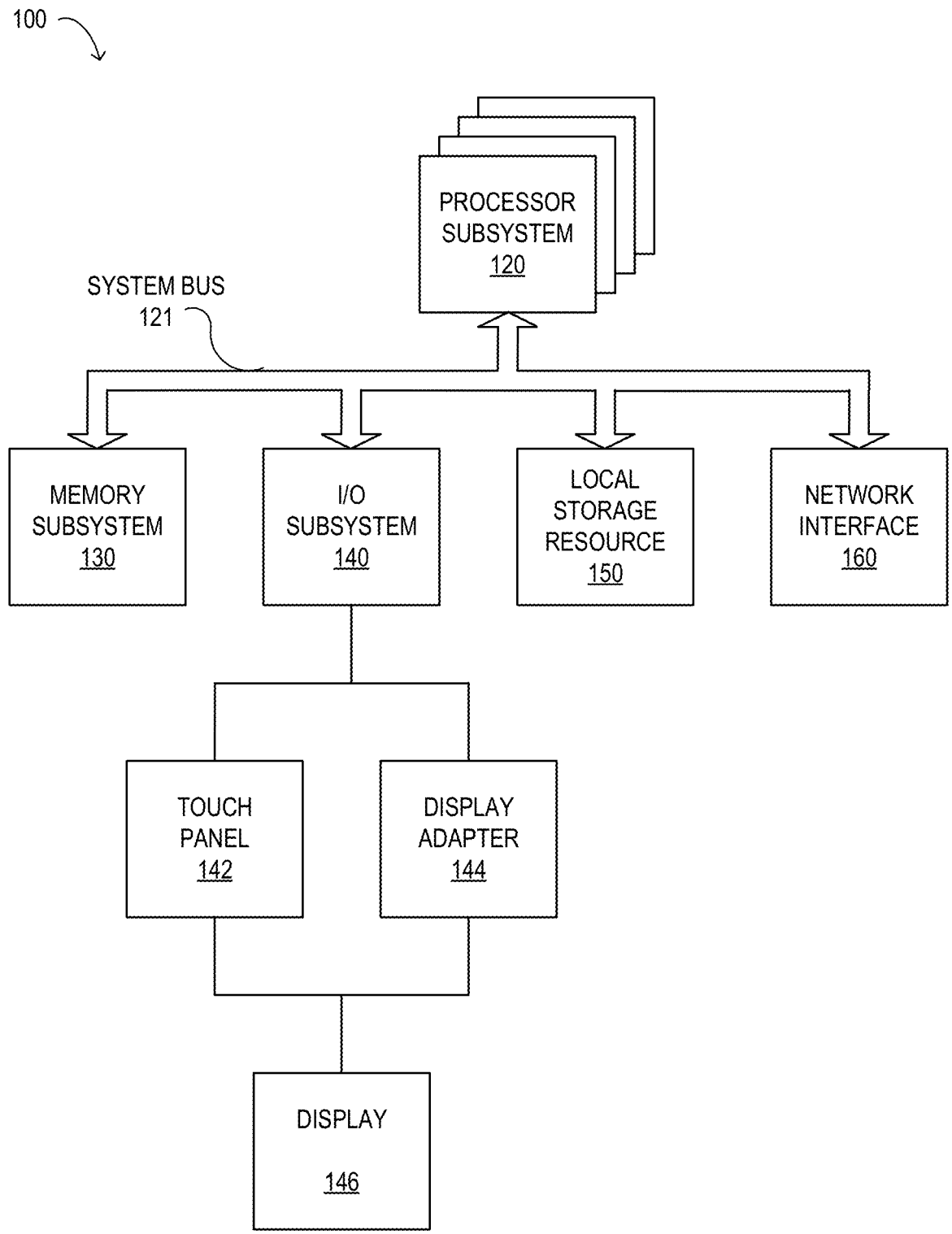
FIG. 1 is a block diagram of selected elements of an embodiment of an information handling system.

DESCRIPTION OF PARTICULAR
EMBODIMENT(S)

In the following description, details are set forth by way of example to facilitate discussion of the disclosed subject matter. It should be apparent to a person of ordinary skill in the field, however, that the disclosed embodiments are exemplary and not exhaustive of all possible embodiments.

As used herein, a hyphenated form of a reference numeral refers to a specific instance of an element and the un-hyphenated form of the reference numeral refers to the collective or generic element. Thus, for example, widget "72-1" refers to an instance of a widget class, which may be referred to collectively as widgets "72" and any one of which may be referred to generically as a widget "72."

For the purposes of this disclosure, an information handling system may include an instrumentality or aggregate of instrumentalities operable to compute, classify, process, transmit, receive, retrieve, originate, switch, store, display, manifest, detect, record, reproduce, handle, or utilize various forms of information, intelligence, or data for business, scientific, control, entertainment, or other purposes. For example, an information handling system may be a personal computer, a PDA, a consumer electronic device, a network storage device, or another suitable device and may vary in size, shape, performance, functionality, and price. The information handling system may include memory, one or more processing resources such as a central processing unit (CPU) or hardware or software control logic. Additional components or the information handling system may include one or more storage devices, one or more communications ports for communicating with external devices as well as various input and output (I/O) devices, such as a keyboard, a mouse, and a video display. The information handling system may also include one or more buses operable to transmit communication between the various hardware components.

For the purposes of this disclosure, computer-readable media may include an instrumentality or aggregation of instrumentalities that may retain data and/or instructions for a period of time. Computer-readable media may include, without limitation, storage media such as a direct access storage device (e.g., a hard disk drive or floppy disk), a sequential access storage device (e.g., a tape disk drive), compact disk, CD-ROM, DVD, random access memory (RAM), read-only memory (ROM), electrically erasable programmable read-only memory (EEPROM), and/or flash memory (SSD); as well as communications media such wires, optical fibers, microwaves, radio waves, and other electromagnetic and/or optical carriers; and/or any combination of the foregoing.

Particular embodiments are best understood by reference to FIGS. 1-11 wherein like numbers are used to indicate like and corresponding parts.

Turning now to the drawings, FIG. 1 illustrates a block diagram depicting selected elements of an information handling system 100 in accordance with some embodiments of the present disclosure. In various embodiments, information handling system 100 may represent different types of portable information handling systems, such as, display devices, head mounted displays, head mount display systems, smart phones, tablet computers, notebook computers, media players, digital cameras, 2-in-1 tablet-laptop combination computers, and wireless organizers, or other types of portable information handling systems. In one or more embodiments, information handling system 100 may also represent other types of information handling systems, including desktop computers, server systems, controllers, and microcontroller units, among other types of information handling systems. Components of information handling system 100 may include, but are not limited to, a processor subsystem 120, which may comprise one or more processors, and system bus 121 that communicatively couples various system components to processor subsystem 120 including, for example, a memory subsystem 130, an I/O subsystem 140, a local storage resource 150, and a network interface 160. System bus 121 may represent a variety of suitable types of bus structures, e.g., a memory bus, a peripheral bus, or a local bus using various bus architectures in selected embodiments. For example, such architectures may include, but are not limited to, Micro Channel Architecture (MCA) bus, Industry Standard Architecture (ISA) bus, Enhanced ISA (EISA) bus, Peripheral Component Interconnect (PCI) bus, PCI-Express bus, HyperTransport (HT) bus, and Video Electronics Standards Association (VESA) local bus.

In FIG. 1, network interface 160 may be a suitable system, apparatus, or device operable to serve as an interface between information handling system 100 and a network. Network interface 160 may enable information handling system 100 to communicate over the network using a suitable transmission protocol and/or standard, including, but not limited to, transmission protocols and/or standards enumerated below with respect to the discussion of the network. In some embodiments, network interface 160 may be communicatively coupled via the network to a network storage resource. The network may be implemented as, or may be a part of, a storage area network (SAN), personal area network (PAN), local area network (LAN), a metropolitan area network (MAN), a wide area network (WAN), a wireless local area network (WLAN), a virtual private network (VPN), an intranet, the Internet or another appropriate architecture or system that facilitates the communication of signals, data and/or messages (generally referred to as data). The network may transmit data using a desired storage and/or communication protocol, including, but not limited to, Fibre Channel, Frame Relay, Asynchronous Transfer Mode (ATM), Internet protocol (IP), other packet-based protocol, small computer system interface (SCSI), Internet SCSI (iSCSI), Serial Attached SCSI (SAS) or another transport that operates with the SCSI protocol, advanced technology attachment (ATA), serial ATA (SATA), advanced technology attachment packet interface (ATAPI), serial storage architecture (SSA), integrated drive electronics (IDE), and/or any combination thereof. The network and its various components may be implemented using hardware, software, or any combination thereof.

As depicted in FIG. 1, processor subsystem 120 may comprise a system, device, or apparatus operable to interpret and/or execute program instructions and/or process data, and may include a microprocessor, microcontroller, digital signal processor (DSP), application specific integrated circuit (ASIC), or another digital or analog circuitry configured to interpret and/or execute program instructions and/or process data. In some embodiments, processor subsystem 120 may interpret and/or execute program instructions and/or process data stored locally (e.g., in memory subsystem 130 and/or another component of information handling system). In the same or alternative embodiments, processor subsystem 120 may interpret and/or execute program instructions and/or process data stored remotely (e.g., in a network storage resource, not shown).

Also in FIG. 1, memory subsystem 130 may comprise a system, device, or apparatus operable to retain and/or retrieve program instructions and/or data for a period of time (e.g., computer-readable media). Memory subsystem 130 may comprise random access memory (RAM), electrically erasable programmable read-only memory (EEPROM), a PCMCIA card, flash memory, magnetic storage, opto-magnetic storage, and/or a suitable selection and/or array of volatile or non-volatile memory that retains data after power to its associated information handling system, such as system 100, is powered down.

In information handling system 100, I/O subsystem 140 may comprise a system, device, or apparatus generally operable to receive and/or transmit data to/from/within information handling system 100. I/O subsystem 140 may represent, for example, a variety of communication interfaces, graphics interfaces, video interfaces, user input interfaces, and/or peripheral interfaces. In various embodiments, I/O subsystem 140 may be used to support various peripheral devices, such as a touch panel, a display adapter, a keyboard, an accelerometer, a touch pad, a gyroscope, an IR sensor, a microphone, a sensor, or a camera, or another type of peripheral device. As shown, I/O subsystem 140 may comprise touch panel 142 and display adapter 144. Touch panel 142 may include circuitry for enabling touch functionality in conjunction with display 146 that is driven by display adapter 144.

Local storage resource 150 may comprise computer-readable media (e.g., hard disk drive, floppy disk drive, CD-ROM, and/or other type of rotating storage media, flash memory, EEPROM, and/or another type of solid state storage media) and may be generally operable to store instructions and/or data. Likewise, the network storage resource may comprise computer-readable media (e.g., hard disk drive, floppy disk drive, CD-ROM, and/or other type of rotating storage media, flash memory, EEPROM, and/or other type of solid state storage media) and may be generally operable to store instructions and/or data. In system 100, I/O subsystem 140 may comprise a system, device, or apparatus generally operable to receive and/or transmit data to/from/within system 100. In addition to local storage resources 150, in some embodiments, information handling system 100 may communicatively couple via network 165 to a network storage resource (not shown) using network interface 160 discussed below.

Network interface 160 may be a suitable system, apparatus, or device operable to serve as an interface between information handling system 100 and network 165. Network interface 160 may enable information handling system 100 to communicate over a network using any suitable transmission protocol and/or standard, including, but not limited to various transmission protocols and/or standards. The network coupled to network interface 160 may be implemented as, or may be a part of, a storage area network (SAN), personal area network (PAN), local area network (LAN), a metropolitan area network (MAN), a wide area network (WAN), a wireless local area network (WLAN), a virtual private network (VPN), an intranet, the Internet or another appropriate architecture or system that facilitates the communication of signals, data and/or messages (generally referred to as data or information). In some embodiments, the network communicatively coupled to network interface 160 may transmit data using a desired storage and/or communication protocol, including, but not limited to, Fibre Channel, Frame Relay, Asynchronous Transfer Mode (ATM), Internet protocol (IP), other packet-based protocol, small computer system interface (SCSI), Internet SCSI (iSCSI), Serial Attached SCSI (SAS) or another transport that operates with the SCSI protocol, advanced technology attachment (ATA), serial ATA (SATA), advanced technology attachment packet interface (ATAPI), serial storage architecture (SSA), integrated drive electronics (IDE), and/or any combination thereof. The network, network interface 160, and/or various components associated therewith may be implemented using hardware, software, or any combination thereof. Network interface 160 may enable wired and/or wireless communications to and/or from information handling system 100.

As noted previously, an information handling system may include a head mounted display device. A head mounted display may comprise a head mounted virtual reality display, a head mounted augmented reality display, a head mounted mixed reality display, night vision googles, an industrial application head mounted display, and a military application head mounted display, or another type of head mounted display. A Typical head mounted display includes a display device and straps coupled to the display device to allow the head mounted display to be worn by a user. When the user wears the head mounted display on their head, the user needs to place the head mounted display on their head so that the user is able to see the display device. Once the head mounted display is in the proper position to see the display device, the user manually adjusts the straps to provide a secure and comfortable fit on the user's head. This adjustment process may not be intuitive and may take a significant amount of time for the user to achieve the desired fit. For example, the adjustment process may take between 2 minutes and 5 minutes to complete depending on the user. If the head mounted display is to be shared and worn by multiple users, each user may need to adjust the straps again to achieve the user's desired fit.

As will be described in further detail herein, the inventors of the present disclosure have discovered methods and systems for automatic adjustment of head mounted display straps of a head mounted display. The head mounted display utilizes eye tracking data from the display device, pressure sensor data around the head mounted display, and strap position data of the head mounted display straps to automatically adjust the head mounted display straps to a user's previously recorded desired fit. Utilizing pressure sensor data instead of mechanical latch placement data provides a continuously reliable fit for the users even when the user's head may have physically changed, such as, for example, when the user is wearing a head cover or headwear, the user's hair style has changed, the length of the user's hair has changed, or another type of physical change.

Figure 2B:
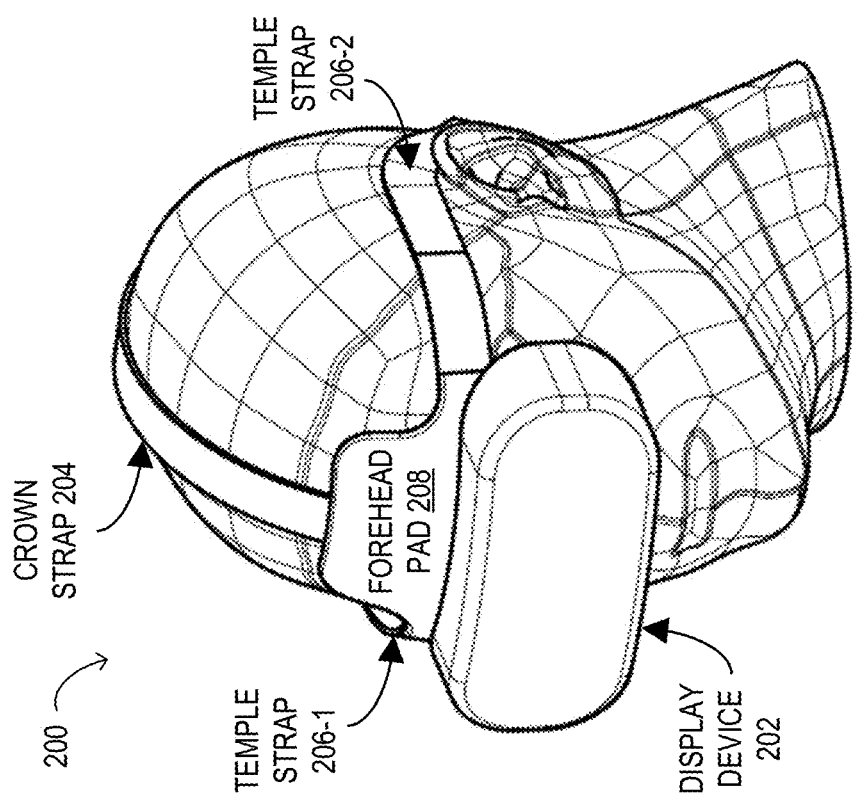
Figure 2A:
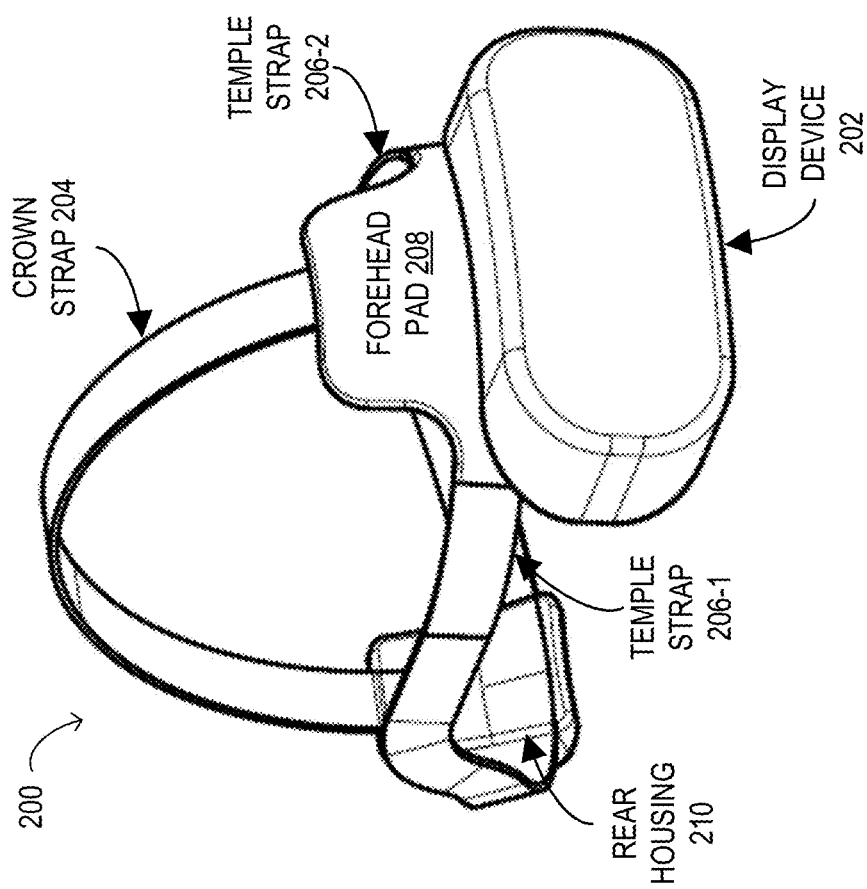

FIGS. 2A, 2B, 2C, 2D, and 2E are various views of selected elements of embodiments of a head mounted display 200. FIG. 2A depicts a first side three quarter view of selected elements of head mounted display 200. In FIG. 2B, a second side three quarter view of selected elements of head mounted display 200 on a head of a user is shown. The second side three quarter view of head mounted display 200 is generally opposite of the first side three quarter view of head mounted display 200 shown in FIG. 2A. FIG. 2C shows a top view of head mounted display 200. In FIG. 2D, a front view of head mounted display 200 is shown. FIG. 2E shows a side view of head mounted display 200. As shown in FIGS. 2A, 2B, 2C, 2D, and 2E head mounted display 200 includes a display device 202, a plurality of straps including a crown strap 204, a temple strap 206-1, and a temple strap 206-2, a forehead pad 208, and a rear housing 210. Forehead pad 208 may be coupled to display device 202 proximate a top side of display device 202. Crown strap 204 may include a first end coupled to display device 202 proximate a top center portion of display device 202 and a second end coupled to rear housing 210 proximate a top center portion of rear housing 210. Temple strap 206-1 may include a first end coupled to forehead pad 208 proximate a first side of display device 202 and a second end coupled to rear housing 210 proximate a first side of rear housing 210. Temple strap 206-2 may include a first end coupled to forehead pad 208 proximate a second side of display device 202 opposite the first side of display device 202 and a second end coupled to rear housing 210 proximate a second side of rear housing 210 opposite the first side of rear housing 210. Head mounted display 200 may also include at least one eye tracking sensor disposed in display device 202, a plurality of pressure sensors disposed around head mounted display 200, a plurality of strap position sensors disposed around head mounted display device, and at least one adjustment actuator of rear housing 210 coupled to the plurality of straps. The plurality of pressure sensors may be associated with the plurality of straps. Each of the plurality of strap position sensors may be associated with a respective strap of the plurality of straps. Head mounted display 200 may also include one or more user input interfaces such as user input interfaces of an information handling system 100 coupled to head mounted display 200, buttons disposed in head mounted display 200, a voice recognition device, a gesture recognition device, a motion detection device, an adjustment input device, or another type of user input interface device, that a user may use to provide user input data and commands to head mounted display device. In one or more embodiments, head mounted display 200 may also be coupled to an information handling system such as information handling system 100.

A user may initiate an initial head mounted display adjustment process disclosed herein, also referred herein as an adjustment process, to adjust head mounted display 200 to properly fit the user. In some embodiments, the user may initiate the adjustment process by placing head mounted display 200 on their head and providing user input, such as a user input command, to head mounted display 200 using at least one of the user input interfaces to begin the adjustment process. For example, the user may enter a command on the information handling system 100, the user may push a button, use a voice command, or perform a hand gesture to initiate the adjustment process. In one or more other embodiments, head mounted display 200 may automatically initiate the adjustment process by detecting when the user places head mounted display 200 on their head.

In one or more embodiments, prior to the authentication process, the user may have initiated a registration process and provided registration information during the registration process to register the user as a valid user of head mounted display 200. During the adjustment process, head mounted display 200 may authenticate the user using an authentication process and one or more authentication devices coupled to head mounted display 200. The authentication process may collect authentication information associated with the user using one or more of IRIS recognition by an IRIS recognition device, facial recognition by a facial recognition device, finger recognition by a finger recognition device, retina recognition by a retina recognition device, voice recognition by a voice recognition device, username and password by an username and password verification device. Once the authentication information has been collected, the authentication process may determine whether the gathered authentication information associated with the user matches the registration information associated with the user. When the authentication information matches the registration information, the user is authenticated.

During the adjustment process, head mounted display 200 may determine whether the plurality of straps are in a release position using each of the plurality of strap position sensors. If head mounted display 200 determines that the plurality of straps are not in the release position, head mounted display 200 move the plurality of straps to the released position using the at least one adjustment actuator. Next, head mounted display 200 may monitor eye location data of at least one eye of the user using the at least one eye tracking sensor while the user manually adjusts head mounted display 200 so that display device 202 is on their face and in front of their eyes. Head mounted display 200 may direct the user to move display device 202 of head mounted display 200 to achieve a clear image being displayed on display device 202 based on the monitored eye location data. Once the user indicates that the user is able to see the clear image displayed by display device 202, head mounted display 200 may capture the monitored eye location data. The user may indicate that they are able to see the clear image by using one of the user input interfaces.

Head mounted display 200 may also monitor strap pressure data associated with the plurality of straps using the plurality of the pressure sensors and strap position data of each respective strap of the plurality of straps using each of the plurality of strap position sensors. Head mounted display 200 may direct the user to adjust the position of each strap to achieve a comfortable and acceptable fit. Head mounted display 200 may adjust the position of each strap of the plurality of straps using the at least one adjustment actuator based on user input provided by the user, monitored strap pressure data, and monitored strap position data of each strap to achieve an acceptable fit of the head mounted display 200 on the user's head. The user may use one or more user input interfaces to provide one or more user input commands to head mounted display 200. For example, the user may push a first directional button associated with crown strap 204 to tighten crown strap 204 or to loosen crown strap 204. The user may also push a second directional button associated with temple straps 206 to tighten temple straps 206 or to loosen temple straps 206. In one or more embodiments, head mounted display 200 may direct the user to move their head to determine whether the movement of the user's head causes movement of head mounted display 200 on the user's head or maintains its position based on at least one of user input, changes in strap pressure data associated with the plurality of straps, detection of movement of head mounted display 200 on the user's head by various motion sensors, or other movement detection mechanisms. If head mounted display 200 determines that the movement of the user's head causes movement of head mounted display 200 on the user's head, head mounted display 200 may direct the user to further tighten the plurality of straps until head mounted display 200 maintains its position on the user's head. Once the user indicates that an accepted fit of head mounted display 200 on the user's head has been achieved, head mounted display 200 may capture the monitored strap pressure data and the monitored strap position data of each respective strap of the plurality of straps. The user may indicate that the accepted fit has been achieved by using one of the user input interfaces. When both the clear image and the accepted fit have been achieved, head mounted display 200 may create a user fit profile including user fit information associated with the user. The user fit information may describe accepted eye location data, accepted strap pressure data, and accepted strap position data of each strap of the head mounted display associated with the user. Head mounted display 200 may record the monitored eye location data, the monitored strap pressure data, and the monitored strap position data of each strap at the accepted eye location data, the accepted strap pressure data, and the accepted strap position data of each strap respectively at the user fit information of the user fit profile associated with the user.

A user may place head mounted display 200 on their head that initiates a subsequent adjustment process to adjust head mounted display 200 to properly fit the user. During the subsequent process, head mounted display 200 may determine whether the plurality of straps is in the released position. If head mounted display 200 determines that the plurality of straps are not in the release position, head mounted display 200 may move the plurality of straps to the released position. In one or more embodiments, head mounted display 200 may authenticate the user using the authentication process as previously described. In one or more embodiments, head mounted display 200 may identify user fit information associated with the user based on the authentication process. In some embodiments, a user may select a previously recorded user fit profile including the user fit information from a list of previously recorded user fit profiles associated with the user presented to the user by head mounted display 200 or information handling system 100. For example, the user may select the user fit profile from the list of previously recorded user fit profiles using one of the user input interfaces. In one or more other embodiments, head mounted display 200 may identify the user fit information associated with the user based on whether the user fit information exists or not. If head mounted display 200 fails to identify the user fit information associated with the user, determines that the user fit information does not exist, or the user has not selected a user fit profile, head mounted display 200 may initiate the initial head mounted display adjustment process described above. When the user fit information associated with the user has been identified or selected, head mounted display 200 may monitor eye location data of at least one eye of the user using the at least one eye tracking sensor. Next, head mounted display 200 may direct the user to move head mounted display 200 such that display device 202 is on their face and in front of their eyes to achieve a desired image being displayed by display device 202 based on the monitored eye location data and the accepted eye location data of the user fit information. Once the user indicates that the user is able to see the desired image displayed by display device 202, head mounted display 200 may capture the monitored eye location data.

Head mounted display 200 may also monitor strap pressure data associated with the plurality of straps using the plurality of the pressure sensors and strap position data of each respective strap of the plurality of straps using each of the plurality of strap position sensors. Head mounted display 200 may automatically adjust the position of each strap using the at least one adjustment actuator to achieve a desired fit of head mounted display 200 worn by the user based on the monitored strap pressure data, the accepted strap pressure data of the user fit information, the monitored strap position data of each strap, and the accepted strap position data of each strap of the user fit information. If head mounted display 200 determines that the monitored strap position data of each strap is different than and no longer matches the accepted strap position data of each strap of the user fit information, head mounted display 200 may update the accepted strap position data of each strap of the user fit information with the monitored strap position data at the user fit information of the user fit profile associated with the user. Alternatively, head mounted display 200 may update the accepted strap position data of each strap of the user fit information with the monitored strap position data and store the updated information at the user fit information of a new user fit profile associated with the user based on user input. The monitored strap position data of each strap may be different than the accepted strap position data of each strap when the user's head may have physically changed, such as, for example, when the user is wearing a head cover or headwear, the user's hair style has changed, the length of the user's hair has changed, or another type of physical change has occurred.

In one or more embodiments, head mounted display 200 may also receive user input which indicates that the accepted fit of head mounted display 200 on the user is to be updated. Head mounted display 200 may direct the user to move head mounted display 200 such that display device 202 is on their face and in front of their eyes to achieve an updated desired image being displayed by display device 202 based on monitored eye location data. Once the user indicates that the updated desired image displayed by display device 202 has been achieved, head mounted display 200 may capture the updated monitored eye location data. Next, head mounted display 200 may adjust the position of each strap of the plurality of straps to achieve an updated fit based on monitored strap pressure data of each strap. Once the user indicates that an updated accepted fit of head mounted display 200 on the user's head has been achieved, head mounted display 200 may capture the updated monitored strap pressure data and the updated monitored strap position data of each respective strap of the plurality of straps. When both the updated desired image and the updated accepted fit have been achieved, head mounted display 200 may update and record the updated monitored eye location data, the updated monitored strap pressure data, and the updated monitored strap position data of each strap at the accepted eye location data, the accepted strap pressure data, and the accepted strap position data of each strap respectively at the user fit information of the user fit profile associated with the user. Alternatively, head mounted display 200 may update the accepted eye location data, the accepted strap pressure data, and the accepted strap position data of each strap respectively of the user fit information with the updated monitored eye location data, the updated monitored strap pressure data, and the updated monitored strap position data of each strap at the user fit information of a new user fit profile associated with the user based on user input.

In one or more embodiments, head mounted display 200 may also monitor context information including movement data associated with head mounted display 200. When the monitored context information indicates that the accepted fit of head mounted display 200 on the user is to be changed, head mounted display 200 may adjust the position of each strap of the plurality of straps to achieve an updated fit based on the monitored strap pressure data of each strap and the monitored context information. The updated fit may be within an operational range of head mounted display 200 that is greater than or equal to a loose fit threshold and less than or equal to a tight fit threshold. The loose fit threshold may be based on a fixed limit that the position of each strap may be loosened to and a lower limit of strap pressure data of each strap to reduce or prevent movement of head mounted display 200 on the user's head. The tight fit threshold may be based on a fixed limit that the position of each strap may be tightened to and a higher limit of strap pressure data of each strap to prevent damage of head mounted display 200 on the user's head. The monitored context information may also indicate that the accepted fit of head mounted display 200 on the user is to be changed based on one or more of a motion sensor of head mounted display 200 that detects that movement of head mounted display 200 has exceeded a high movement change threshold, the motion sensor that detects that movement of head mounted display 200 has decreased below a low movement change threshold, an activity indicator may be received that indicates that movement of head mounted display 200 is to exceed the high movement change threshold, an activity indicator may be received that indicates that movement of head mounted display 200 is to decrease below the low movement change threshold, the monitored strap pressure data that indicates the desired fit of head mounted display 200 on the user has changed such that the desired fit is outside the operational range of head mounted display 200, and a simultaneous localization and mapping (SLAM) subsystem that indicates movement of head mounted display 200 is to change. For example, the activity indicator may indicate that the user is about to start a high activity game and may require head mounted display 200 to proactively tighten the plurality of straps to prevent or minimize movement of head mounted display 200 on the user's head. In another example, the activity indicator may indicate that the user is about to start watching a movie and may allow head mounted display 200 to proactively loosen the plurality of straps due to a much-reduced movement of the user's head. The SLAM subsystem may provide localization and mapping of a user's environment including surface information, depth information, distance information of objects surrounding the user, and other types of environmental information and conditions, or combinations thereof.

Figure 3B:
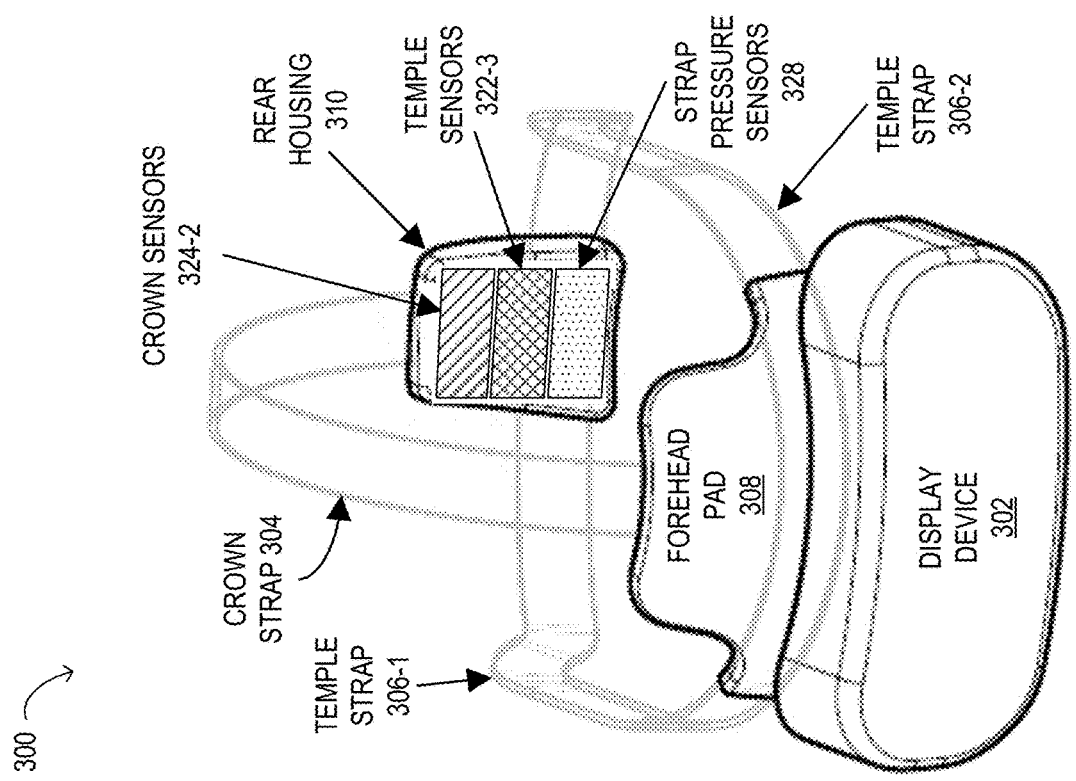
FIGS. 3A and 3B are various three-quarter views of selected elements of an embodiment of a head mounted display.
Figure 3A:
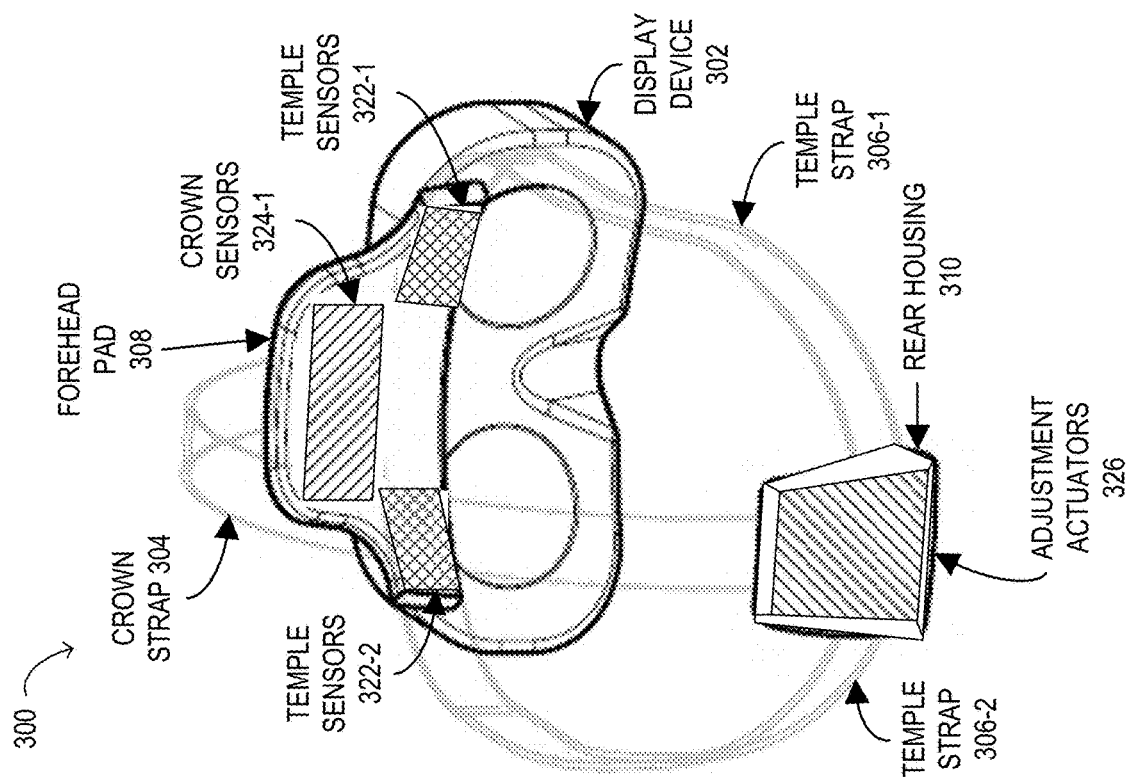

FIGS. 3A and 3B are three quarter views of selected elements of an embodiment of a head mounted display 300. Head mounted display 300 is structurally and functionally similar to head mounted display 200 described above with reference to FIG. 2A. In FIG. 3A, a back side three quarter view of head mounted display 300 is depicted. As shown in FIG. 3A, head mounted display 300 includes a display device 302, a crown strap 304, a temple strap 306-1, a temple strap 306-2, a forehead pad 308, a rear housing 310, temple sensors 322-1, temple sensors 322-2, crown sensors 324, and adjustment actuators 326. As shown in FIG. 3A, temple sensors 322-1 are disposed within forehead pad 308 proximate a first side of forehead pad 308 and a first end of temple strap 306-1. In one or more embodiments, temple sensors 322-1 may be disposed within the first end of temple strap 306-1, or one or more other suitable locations within head mounted display 300. In FIG. 3A, temple sensors 322-2 are shown as being disposed within forehead pad 308 proximate a second side of forehead pad 308 and a first end of temple strap 306-2. The second side of forehead pad 308 is shown generally opposite the first side of forehead pad 308. In one or more other embodiments, temple sensors 322-2 may be disposed within the first end of temple strap 306-2, or one or more other suitable locations within head mounted display 300. As shown in FIG. 3A, crown sensors 324-1 are disposed within forehead pad 308 proximate a middle top side of forehead pad 308 and a first end of crown strap 304. In one or more other embodiments, crown sensors 324-1 may be disposed within the first end of crown strap 304, or one or more other suitable locations within head mounted display 300. In FIG. 3A, adjustment actuators 326 are shown disposed within rear housing 310 proximate a second end of temple strap 306-1, a second end of temple strap 306-2, and a second end of crown strap 304. In one or more other embodiments, adjustment actuators 326 may be disposed within the second end of temple strap 306-1, the second end of temple strap 306-2, the second end of crown strap 304, or combinations thereof, or one or more other suitable locations within head mounted display 300.

In FIG. 3B, a front side three quarter view of head mounted display 300 is depicted. As shown in FIG. 3B, head mounted display 300 also includes temple sensors 322-3, crown sensors 324-2, and strap pressure sensors 328. In FIG. 3B, temple sensors 322-3 are shown disposed within rear housing 310 proximate the second end of temple strap 306-1 and the second end of temple strap 306-2. In one or more other embodiments, temple sensors 322-3 may be disposed within the second end of temple strap 306-1, the second end of temple strap 306-2, or combinations thereof, or one or more other suitable locations within head mounted display 300. In FIG. 3B, crown sensors 324-2 are shown disposed within rear housing 310 proximate the second end of crown strap 304. In one or more other embodiments, crown sensors 324-2 may be disposed within the second end of crown strap 304 or one or more other suitable locations within head mounted display 300. In FIG. 3B, strap pressure sensors 328 are shown disposed within rear housing 310 proximate the second end of crown strap 304. In one or more other embodiments, strap pressure sensors 328 may be disposed within the second end of crown strap 304, the second end of temple strap 306-1, the second end of temple strap 306-2, or combinations thereof, or one or more other suitable locations within head mounted display 300.

Figure 4:
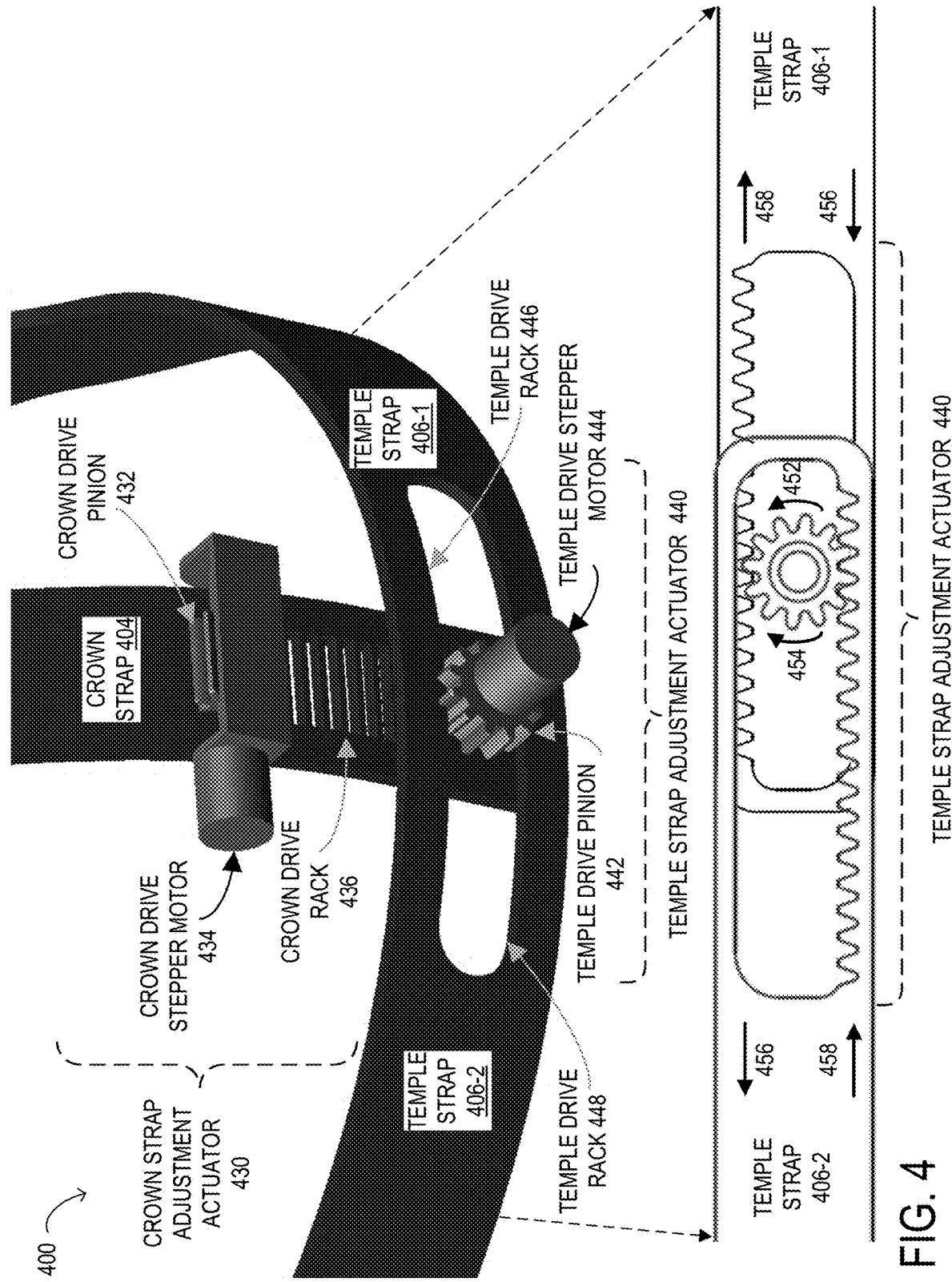
FIG. 4 is a three quarter view of selected elements of an embodiment of a head mounted display including a crown strap actuator and a temple strap actuator.

FIG. 4 is a partial back side three quarter view of selected elements of an embodiment of a head mounted display 400 including a crown strap actuator and a temple strap actuator. Head mounted display 400 is structurally and functionally similar to head mounted display 200 described above with reference to FIG. 2A. As shown in FIG. 4, head mounted display 400 includes a crown strap 404, a temple strap 406-1, a temple strap 406-2, a crown strap actuator 430, and a temple strap actuator 440. Crown strap actuator 430 includes a crown drive pinion 432, a crown drive stepper motor 434, and a crown drive rack 436 disposed in crown strap 404. Temple strap actuator 440 includes a temple drive pinion 442, a temple drive stepper motor 444, a temple drive rack 446 disposed in temple strap 406-1, and a temple drive rack 448 disposed in temple strap 406-2. A plurality of strap position sensors associated with crown strap 404 may be disposed in at least one of crown strap adjustment actuator 430, crown strap 404, combination thereof, or another suitable place within head mounted display 400. Another plurality of strap position sensors associated with each temple strap 406 of temple straps 406-1 and 406-2 may be disposed in at least one of temple strap adjustment actuator 440, temple strap 406-1, temple strap 406-2, or combinations thereof, or another suitable place within head mounted display 400.

In operation, head mounted display 400 may monitor the plurality of strap position sensors associated with each strap and adjust the position of each strap. When the position of crown strap 404 is to be adjusted to increase the pressure of crown strap 404 to achieve a desired fit of head mounted display 200, crown strap adjustment actuator 430 may utilize crown drive stepper motor 434 to rotate crown drive pinion 432 in a first rotational direction to cause crown drive pinion 432 to move in a first direction along crown drive rack 436 to tighten crown strap 404. When the position of crown strap 404 is to be adjusted to decrease the pressure of crown strap 404, crown strap adjustment actuator 430 may utilize crown drive stepper motor 434 to rotate crown drive pinion 432 in a second rotational direction to cause crown drive pinion 432 to move in a second direction along crown drive rack 436 to loosen crown strap 404. The second rotational direction may be opposite the first rotational direction and the second direction may be opposite the first direction.

When the positions of temple straps 406-1 and 406-2 are to be adjusted to increase the pressure of temple straps 406 to achieve a desired fit of head mounted display 200, temple strap adjustment actuator 440 may utilize temple drive stepper motor 444 to rotate temple drive pinion 442 in a rotational direction 452 to cause temple drive rack 446 to move in a direction 456 and temple drive rack 448 to move in a direction 458 to tighten temple straps 406-1 and 406-2. When the position of temple straps 406-1 and 406-2 are to be adjusted to decrease the pressure of temple straps 406, temple strap adjustment actuator 440 may utilize temple drive stepper motor 444 to rotate temple drive pinion 442 in a rotational direction 454 to cause temple drive rack 446 to move in direction 458 and temple drive rack 448 to move in direction 456 to loosen temple straps 406-1 and 406-2.

Rotational direction may be opposite the first rotational direction and the second direction may be opposite the first direction.

FIG. 5 is a front view of selected elements of an embodiment of a head mounted display 500 on a head of a user. Head mounted display 500 is structurally and functionally similar to head mounted display 200 described above with reference to FIG. 2A. As shown in FIG. 5, head mounted display 500 includes a display device 502 having alignment directions 562. During operation, head mounted display 500 may direct the user to move head mounted display 500 such that display device 502 is on their face and in front of their eyes to achieve a desired image being displayed by display device 502 based on the monitored eye location data and the accepted eye location data of the user fit information, as previously described with reference to FIG. 2A. In response to being directed by head mounted display 500, the user may move display device 502 back and forth, up and down, rotate display device 502 clock wise, or rotate display device 502 counter clock wise as indicated by alignment directions 562, or combinations thereof, to ensure display device 502 is in the proper position on their face and in front of their eyes to achieve the desired image.

FIG. 6 is a rear view of selected elements of an embodiment of a display device 602 of a head mounted display 600. Head mounted display 600 is structurally and functionally similar to head mounted display 200 described above with reference to FIG. 2A. As shown in FIG. 6, display device 602 includes an eye tracking sensor 672-1, an eye tracking sensor 672-2, an eye tracking sensor region 674-1, an eye tracking sensor region 674-2, alignment crosshairs 676-1, alignment crosshairs 676-2, an alignment marker 678-1, and an alignment marker 678-2. Eye tracking sensor 672-1, eye tracking sensor region 674-1, alignment crosshairs 676-1, and alignment marker 678-1, are associated with a respective eye of a user such as a left eye of the user. Eye tracking sensor 672-2, eye tracking sensor region 674-2, alignment crosshairs 676-2, and alignment marker 678-2, are associated with a respective eye of a user such as a right eye of the user.

During operation, head mounted display 200 may monitor eye location data of each respective eye of the user using the respective eye tracking sensor 672. Head mounted display 600 may direct the user to move head mounted display 600 such that display device 602 is on their face and in front of their eyes to achieve a desired image being displayed by display device 602, as described above with reference to FIG. 2A. While the user is moving display device 602 to the proper position, head mounted display 600 may actively move alignment crosshairs 676-1 and 676-2, and alignment markers 678-1 and 678-2 on display device 602 based on the monitored eye location data and the accepted eye location data of the user fit information. For example, while the user is moving display device 602 towards the proper position, alignment marker 678-1 being displayed on display device 602 may move until the left eye is aligned based on the accepted eye location data of the left eye. When the left eye is aligned based on the accepted eye location data, the small crosshairs on alignment marker 678-1 will be aligned with alignment crosshairs 676-1, which indicates that the left eye is aligned with display device 602. Similarly, alignment marker 678-2 being displayed on display device 602 may move until the right eye is aligned based on the accepted eye location data of the right eye. When the right eye is aligned based on the accepted eye location data, the small crosshairs on alignment marker 678-2 will be aligned with alignment crosshairs 676-2, which indicates that the right eye is aligned with display device 602. When both eyes of user are aligned with display device 602, the user may communicate an indicator to head mounted display 600, as described above with reference to FIG. 2A. The indicator may indicate that the desired image of the displayed image has been achieved when both eyes of the user have been aligned with display device 602.

Figure 7:
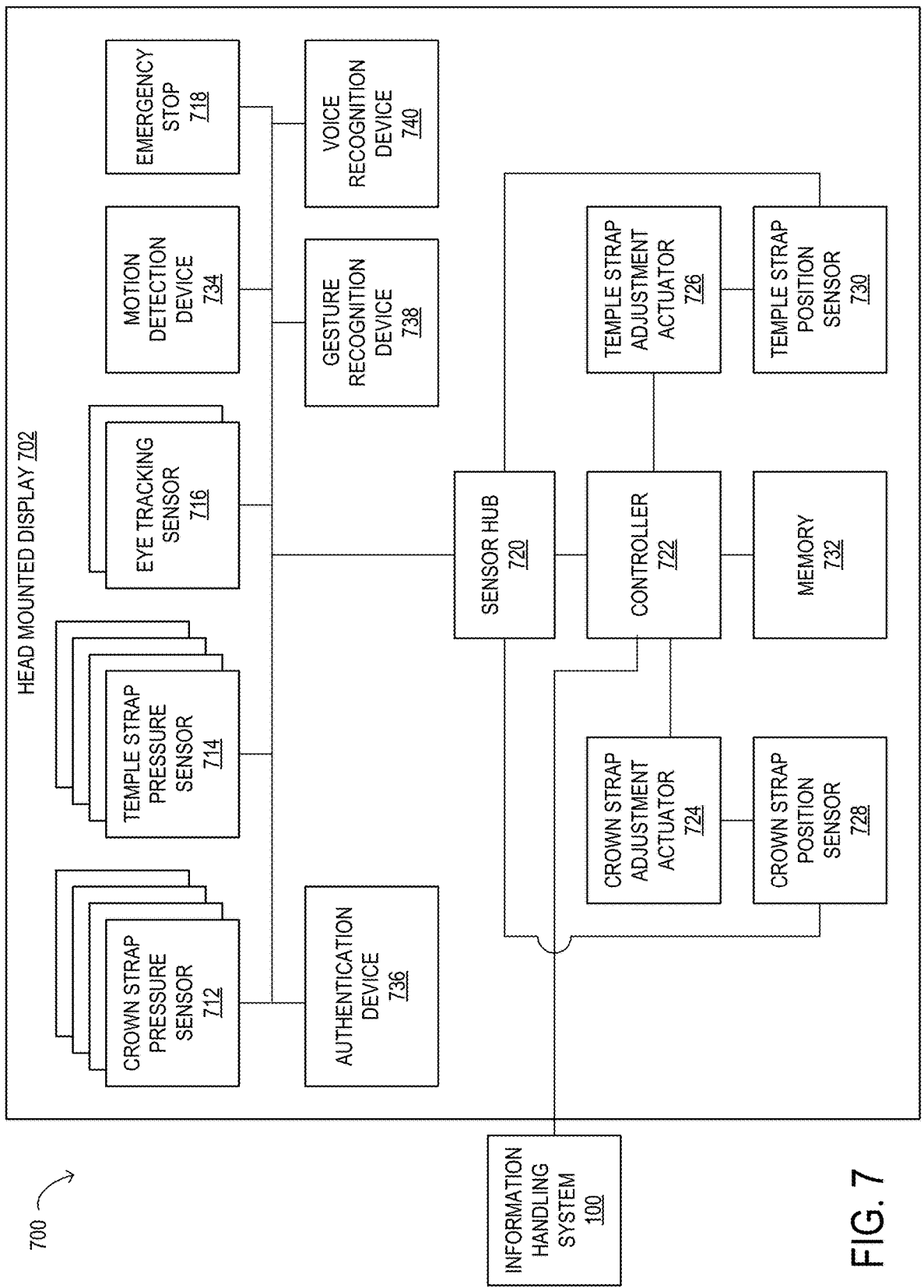
FIG. 7 is a block diagram of selected elements of an embodiment of a head mounted display system including a head mounted display and an information handling system.

FIG. 7 is a block diagram of selected elements of an embodiment of a head mounted display system 700 including a head mounted display 702 and information handling system 100. Head mounted display 702 is functionally similar to head mounted display 200 described above with reference to FIG. 2A. Head mounted display 702 includes one or more crown strap pressure sensors 712, one or more temple strap pressure sensors 714, one or more eye tracking sensors 716, an emergency stop 718, a sensor hub 720, a controller 722, a crown strap adjustment actuator 724, a temple strap adjustment actuator 726, a crown strap position sensor 728, a temple strap position sensor 730, a memory 732, a motion detection device 734, an authentication device 736, a gesture recognition device 738, and a voice recognition device 740 having an audio input device, which may be a microphone. Controller 722 may be functionally similar to information handling system 100 as described above with reference to FIG. 1. Head mounted display 702 may be coupled to information handling system 100 by a wired connection or wirelessly by a wireless communication device. The wireless communication device may be a Bluetooth device, an infrared device, a near field communication device, a Zigbee device, or another type of wireless communication device. In some embodiments, head mounted display 702 may operate as a standalone system that is independent of information handling system 100. In one or more other embodiments, head mounted display 702 may operate cooperatively with information handling system 100 as a complete head mounted display system. In the exemplary head mounted display system, head mounted display 702 and information handling system 100 may perform one or more shared processes, one or more independent processes, or combinations thereof. For example, information handling system 100 may provide content to head mounted display 702 such as a movie to be displayed by head mounted display 702, information handling system 100 and head mounted display 702 may perform shared processes including a user authentication process, an interactive video game with content and real-time feedback, and head mounted display 702 may perform the adjustment process with information communicated between head mounted display 702 and information handling system 100. Information and data may be stored at memory 732 of head mounted display 702, at a memory of memory subsystem 130 of information handling system 100, or combinations thereof. For example, information handling system 100 may store registration information and authentication information associated with each user of head mounted display 702 at the memory of memory subsystem 130 which may be accessed by head mounted display 702. As another example, head mounted display 702 may store a user fit profile and corresponding user fit information including user identification information, accepted eye location data, accepted strap pressure data, and accepted strap position data, at memory 732 of head mounted display 702.

During operation, sensor hub 720 may coordinate the transmission of sensor data and sensor commands between controller 722 and crown strap pressure sensors 712, temple strap pressure sensors 714, eye tracking sensors 716, crown strap position sensor 728, temple strap position sensor 730, emergency stop 718, a motion detection device 734, an authentication device 736, a gesture recognition device 738, and a voice recognition device 740. Emergency stop 718 may include a hardware emergency stop, a software emergency stop, or another type of emergency stop that may allow controller 722 to stop operation of head mounted display 702 to prevent any damage from occurring. When controller 722 detects an unexpected or abnormal condition during operation of head mounted display 702, controller 722 may move the straps of head mounted display 702 to the released position and initiate an emergency stop process using emergency stop 718. For example, controller 722 may detect that the eyes of a user are not in the expected position, abnormal pressure sensor data may be detected by at least one of crown strap pressure sensors 712 and temple strap pressure sensors 714, or abnormal strap position data may be detected by at least one of crown strap position sensor 728 and temple strap position sensor 730. Controller 722 may perform a user registration process, an authentication process using authentication device 736, process user input and commands using one or more of motion detection device 734 to capture and interpret a user's head motions, gesture recognition device 738 to capture and interpret a user's gestures, and voice recognition device 740 to capture and interpret a user's voice input, identify a user, an initial adjustment process, subsequent adjustment processes, monitor crown strap pressure data associated with the crown strap using crown strap pressure sensors 712, monitor temple strap pressure data associated with the plurality of temple straps using temple strap pressure sensors 714, monitor motion of head mounted display 702 using motion detection device 734, monitor eye location data of at least one eye of the user using eye tracking sensors 716, monitor crown strap position data associated with the crown strap using crown strap position sensors 728, monitor temple strap position data for each respective temple strap using temple strap position sensors 730, direct a user to move head mounted display to achieve a desired image and a desired fit, adjust the position of the crown strap using crown strap adjustment actuator 724, adjust the position of each strap of the plurality of straps using temple strap adjustment actuator 726, record user fit information, update user fit information, handle error conditions and processing, communicate with information handling system 100, among other types of processes and tasks, as previously described.

Figure 8A:
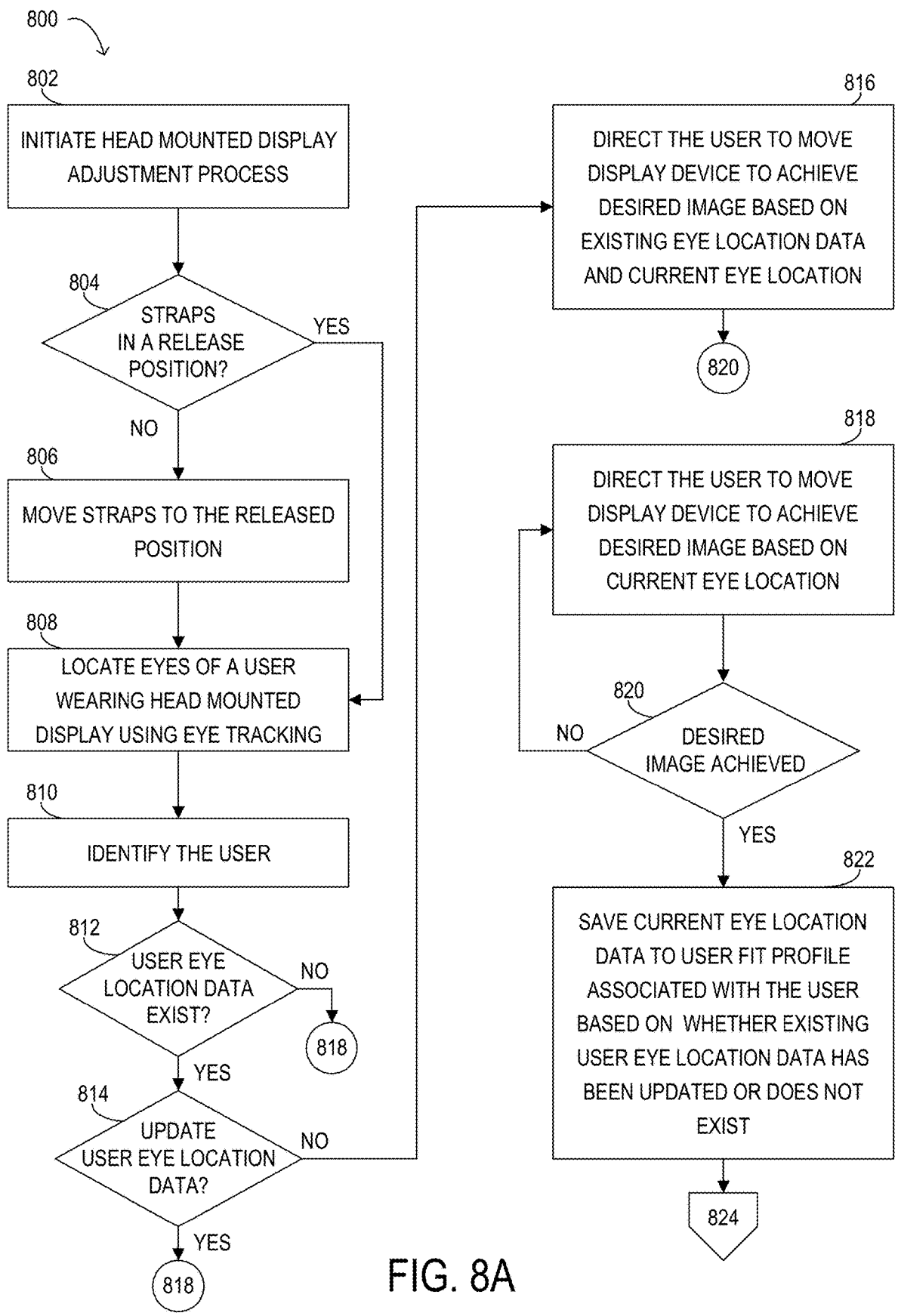
FIGS. 8A and 8B depict a flowchart of selected elements of an embodiment of a method for adjustment of a head mounted display using eye tracking and pressure sensor data associated with straps of the head mounted display.
Figure 8B:
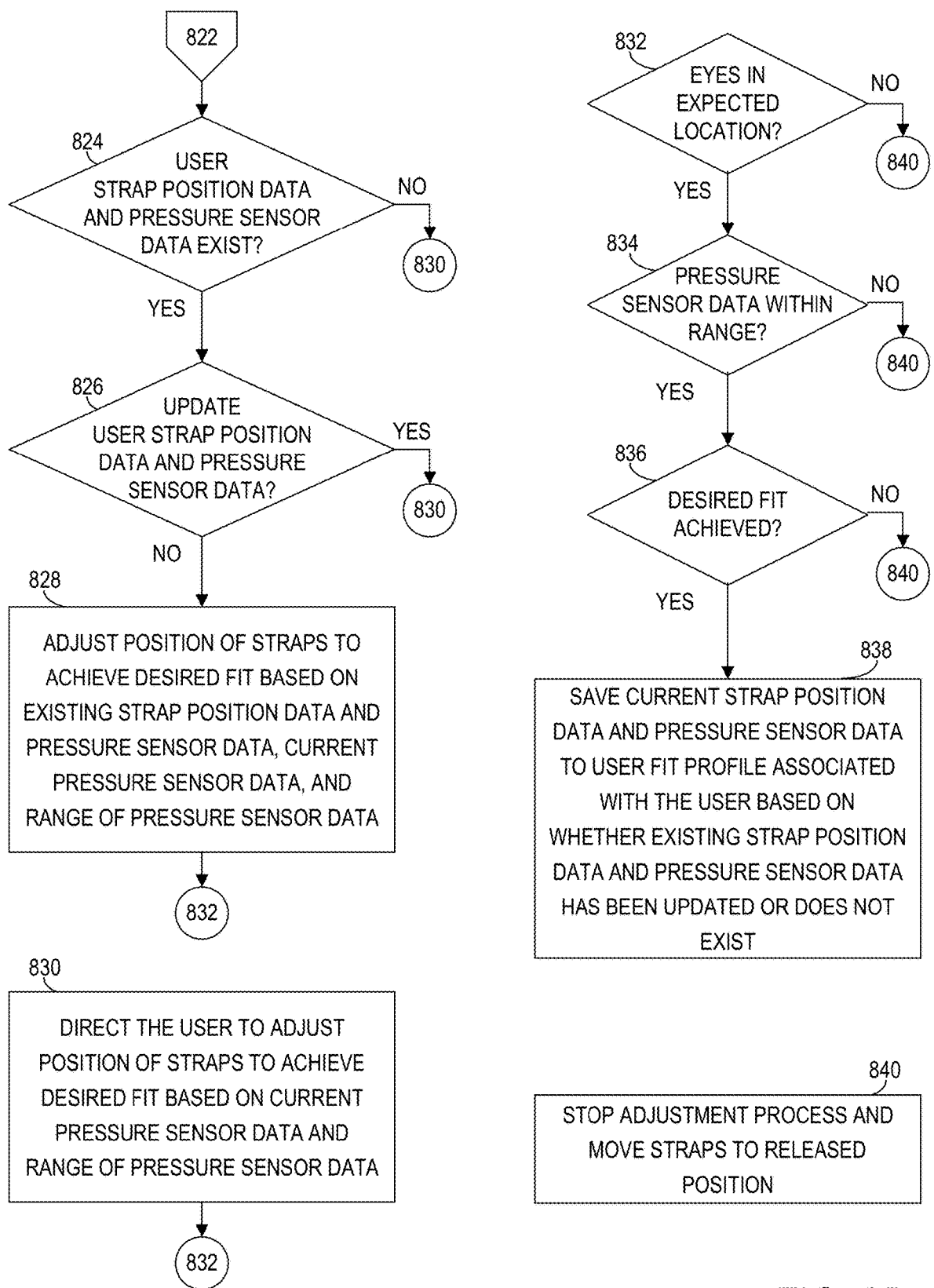

FIGS. 8A and 8B depicts a flowchart of selected elements of an embodiment of a method 800 for adjustment of a head mounted display using eye tracking and pressure sensor data associated with straps of the head mounted display. It is noted that certain operations described in method 800 may be optional or may be rearranged in different embodiments.

Method 800 may begin at step 802, by initiating a head mounted display adjustment process. At step 804, determining, by the head mounted display, whether the straps of the head mounted display are in a released position. When it is determined that the straps of the head mounted display are in the released position, method 800 may proceed to step 808. Otherwise, method 800 may proceed to step 806. At step 806, moving, by the head mounted display, the straps to the released position. At step 808, locating, by the head mounted display, eye location of eyes of a user wearing the head mounted display using eye tracking. At step 810, identifying the user. At step 812, determining, by the head mounted display, whether eye location data associated with the user exists. When it is determined that the eye location data associated with the user exists, method 800 may proceed to step 814. Otherwise, method 800 may proceed to step 818. At step 814, determining, by the head mounted display, whether to update the existing eye location data associated with the user. The head mounted display may determine that the existing eye location data is to be updated based on user input that indicates the data is to be updated. When it is determined to update the existing eye location data associated with the user, method 800 may proceed to step 818. Otherwise, method 800 may proceed to step 816. At step 816, the head mounted display, may direct the user to move display device of the head mounted display to achieve a desired image based on the existing eye location data and current eye location. Method may proceed to step 820. At step 818, the head mounted display, may direct the user to move the display device to achieve the desired image based on the current eye location. At step 820, determining whether the desired image has been achieved. When the desired image has been achieved, method 800 may proceed to step 822. Otherwise, method 800 may proceed back to step 818. At step 822, the head mounted display, saving the current eye location data to a user fit profile associated with the user based on whether existing user eye location data has been updated or does not exist. At step 824, determining, by the head mounted display, whether user strap position data and pressure sensor data associated with the user exists. When it is determined that the user strap position data and pressure sensor data associated with the user exists, method 800 may proceed to step 826. Otherwise, method 800 may proceed to step 830. At step 826, determining, by the head mounted display, whether to update the existing user strap position data and pressure sensor data associated with the user. The head mounted display may determine that the existing user strap position data and pressure sensor data is to be updated based on user input that indicates the data is to be updated. When it is determined to update the existing user strap position data and pressure sensor data associated with the user, method 800 may proceed to step 830. At step 828, adjusting, by the head mounted display, the position of the straps to achieve the desired fit based on the existing user strap position data, existing user pressure sensor data, current pressure sensor data, and a range of pressure sensor data. Method 800 may proceed to step 832. At step 830, the head mounted display may direct the user to adjust the position of the straps to achieve the desired fit based on the current pressure sensor data and the range of pressure sensor data. At step 832, determining, by the head mounted display, whether the eyes are in the expected location. When it is determined that the eyes are in the expected location, method 800 may proceed to step 834. Otherwise, method 800 may proceed to step 840. At step 834, determining, by the head mounted display, whether the pressure sensor data is within range. When it is determined that the pressure sensor data is within range, method 800 may proceed to step 836. Otherwise, method 800 may proceed to step 840. At step 836, determining, by the head mounted display, whether the desired fit has been achieved. When it is determined that the desired fit has been achieved, method 800 may proceed to step 838. Otherwise, method 800 may proceed to step 840. At step 838, saving, by the head mounted display, the current strap position data and the current pressure sensor data to the user fit profile associated with the user based on whether the existing strap position data and the existing pressure sensor data has been updated or does not exist. At step 840, an unexpected or abnormal condition during operation of the head mounted display may have been detected. In response, the head mounted display may stop the head mounted display adjustment process, move the straps of to the released position, and initiate an emergency stop process to stop operation of head mounted display 702 to prevent any damage from occurring. An unexpected or abnormal condition may include the head mounted display detecting that the eyes of a user are not in the expected position, detecting abnormal pressure sensor data by at least one of crown strap pressure sensors and temple strap pressure sensors, or detecting abnormal strap position data by at least one of crown strap position sensor and temple strap position sensor.

Figure 9:
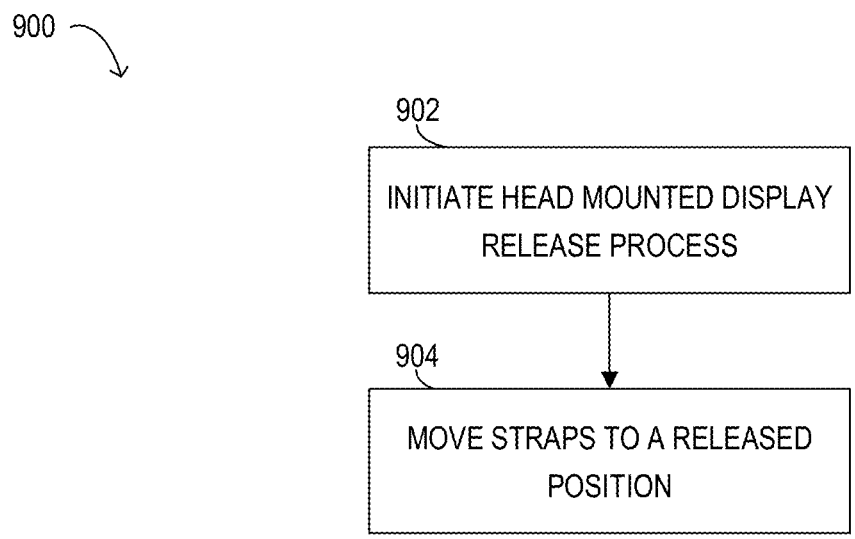
FIG. 9 is flowchart depicting selected elements of an embodiment of a method for moving straps of a head mounted display to a released position.

FIG. 9 is flowchart depicting selected elements of an embodiment of a method 900 for moving straps of a head mounted display to a released position. It is noted that certain operations described in method 900 may be optional or may be rearranged in different embodiments.

Method 900 may begin at step 902, by initiating a head mounted display release process. At step 904, moving the straps to a released position.

Figure 10:
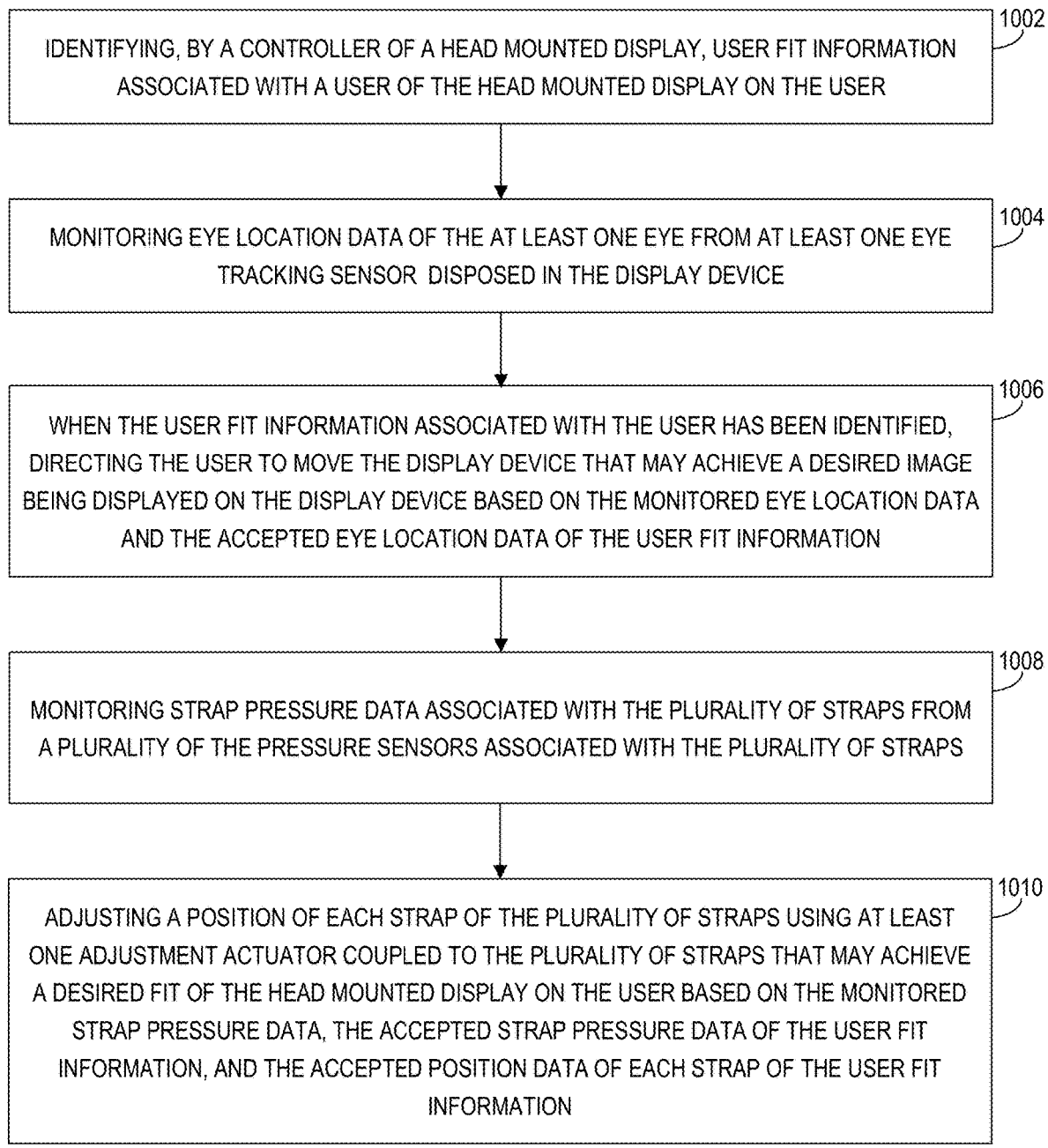
FIG. 10 is flowchart depicting selected elements of an embodiment of a method for automatic adjustment of head mounted display straps of a head mounted display.

FIG. 10 is flowchart depicting selected elements of an embodiment of a method for automatic adjustment of head mounted display straps of a head mounted display. It is noted that certain operations described in method 1000 may be optional or may be rearranged in different embodiments.

Method 1000 may begin at step 1002, by identifying, by a controller of a head mounted display, user fit information associated with a user of the head mounted display on the user. The user fit information may describe accepted eye location data of at least one eye of the user, accepted strap pressure data associated with a plurality of straps coupled to a display device of the head mounted display, and accepted strap position data of each strap of a plurality of straps. At step 1004, monitoring, by the controller, eye location data of the at least one eye using at least one eye tracking sensor disposed in the display device. At step 1006, when the user fit information associated with the user has been identified, directing, by the controller, the user to move the display device that may achieve a desired image being displayed on the display device based on the monitored eye location data and the accepted eye location data of the user fit information. At step 1008, monitoring, by the controller, strap pressure data associated with the plurality of straps using a plurality of the pressure sensors associated with the plurality of straps. At step 1010, automatically adjusting, by the controller, a position of each strap of the plurality of straps using at least one adjustment actuator coupled to the plurality of straps that may achieve a desired fit of the head mounted display on the user based on the monitored strap pressure data, the accepted strap pressure data of the user fit information, and the accepted strap position data of each strap of the user fit information. After step 1010, method 1000 may end.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A head mounted display, comprising:
    a display device;
    at least one eye tracking sensor disposed in the display device;
    a plurality of straps coupled to the display device;
    a plurality of pressure sensors associated with the plurality of straps;
    at least one adjustment actuator coupled to the plurality of straps; and
    a controller configured to:
    monitor eye location data using the at least one eye tracking sensor;
    record the monitored eye location data as accepted eye location data in user fit information associated with a user of the head mounted display;
    capture strap pressure data and strap position data for the plurality of straps;
    store one or more of the captured strap pressure data and the captured strap position data in the user fit information as accepted strap pressure data and accepted strap position data associated with the recorded eye location data;
    monitor strap pressure data associated with the plurality of straps using the plurality of pressure sensors; and
    adjust a position of one or more straps of the plurality of straps using the at least one adjustment actuator based on one or more of the monitored strap pressure data, the accepted strap pressure data stored in the user fit information, the accepted strap position data of the plurality of straps and the accepted eye location data of the user fit information associated with the recorded eye location data.

2. The head mounted display of claim 1, wherein the controller is configured to:
    direct the user to move the display device to achieve the desired image being displayed on the display device;
    adjust the position of one or more straps of the plurality of straps using the at least one adjustment actuator to achieve an accepted fit of the head mounted display on the user based on the monitored strap pressure data; and
    record the monitored eye location data, the monitored strap pressure data, and the adjusted strap position data of each strap at the accepted eye location data, the accepted strap pressure data, and the accepted strap position data of each strap respectively of the user fit information associated with the user.

3. The head mounted display of claim 1, wherein the plurality of straps comprises:
    a crown strap coupled to the display device proximate a top center portion of the display device;
    a first temple strap coupled to the display device proximate a first side portion of the display device; and
    a second temple strap coupled to the display device proximate a second side portion of the display device opposite the first side portion of the display device, wherein the second temple strap is coupled to the crown temple strap and the first temple strap,
    wherein the monitored strap pressure data is determined based on pressure sensor data from the plurality of pressure sensors and strap position data for the crown strap, the first temple strap and the second temple strap.

4. The head mounted display of claim 1, wherein:
    an image being displayed on the display device includes an alignment crosshair and an alignment marker associated with a respective eye of the at least one eye of the user, and
    wherein a desired image is achieved when the alignment marker is aligned with the alignment crosshair associated with the respective eye.

5. The head mounted display of claim 1, wherein:
    the head mounted display further comprises:
        a plurality of strap position sensors, each of the plurality of strap position sensors associated with a respective strap of the plurality of straps, and the controller is configured to:
monitor strap position data of each respective strap of the plurality of straps using each of the plurality of strap position sensors, and
command the at least one adjustment actuator to adjust the position of a respective strap of the plurality of straps based on the strap position data.

6. The head mounted display of claim 1, wherein the controller is configured to:
monitor context information associated with the head mounted display;
when the monitored context information indicates that the accepted fit of the head mounted display on the user is to be changed, adjust the position of one or more straps of the plurality of straps using the at least one adjustment actuator to achieve an updated fit of the head mounted display based on the monitored strap pressure data and the monitored context information,
wherein the updated fit is within an operational range of the head mounted display that is greater than or equal to a loose fit threshold and less than or equal to a tight fit threshold.

7. The head mounted display of claim 6, wherein:
the monitored context information indicates that the accepted fit of the head mounted display on the user is to be changed based on one or more of determining that movement of the head mounted display has exceeded a high movement change threshold, determining that movement of the head mounted display has decreased below a low movement change threshold, receiving an activity indicator that indicates that that movement of the head mounted display is about to exceed the high movement change threshold, the motion sensor indicating that movement of the head mounted display is about to decrease below the low movement change threshold, and the monitored strap pressure data indicating that the desired fit of the head mounted display on the user has changed such that the desired fit is outside the operational range of the head mounted display.

8. The head mounted display of claim 1, wherein the controller is configured to:
authenticate the user using an authentication process and one or more authentication devices coupled to the head mounted display,
wherein the authentication process comprises one or more of IRIS recognition, facial recognition, finger recognition, retina recognition, voice recognition, username and password verification, and
wherein identification of the user fit information associated with the user of the head mounted display is based on the authentication process.

9. The head mounted display of claim 1, wherein the controller is configured to:
command the at least one adjustment actuator to adjust the position of at least one strap of the plurality of straps based on at least one of a hand gesture by the user, a head gesture by the user, a voice command by the user, and adjustment input provided by an adjustment input device of the head mounted display initiated by the user.

10. The head mounted display of claim 1, wherein the at least one adjustment actuator comprises:
a drive pinion;
a drive stepper motor coupled to the drive pinion; and
a drive rack coupled to the drive pinion, the drive rack disposed in at least one strap of the plurality of straps,
wherein the at least one adjustment actuator is configured to:
rotate, using the drive stepper motor, the drive pinion in a first rotational direction to cause the drive pinion to move in a first direction along the drive rack to tighten the at least one strap to increase the pressure of the at least one strap to achieve the accepted fit of the head mounted display; and
rotate, using the drive stepper motor, the drive pinion in a second rotational direction to cause the drive pinion to move in a second direction along the drive rack to loosen the at least one strap to decrease the pressure of the at least one strap to achieve the accepted fit of the head mounted display, and wherein the second rotational direction is opposite the first rotational direction and the second direction is opposite the first direction.

11. A method for automatically adjusting one or more straps in a plurality of straps coupled to a head mounted display, the head mounted display comprising a display device, an eye tracking sensor, a plurality of pressure sensors located around the display device, a plurality of strap position sensors and at least one adjustment actuator, the method comprising:
monitoring, by a controller, eye location data using the eye tracking sensor disposed in the display device;
recording the monitored eye location data in user fit information associated with a user of the head mounted display;
capturing strap pressure data and strap position data for the plurality of straps;
storing one or more of the captured strap pressure data and the captured strap position data in user fit information as accepted strap pressure data and accepted strap position data associated with the recorded eye location data;
monitoring, by the controller, strap pressure data associated with the plurality of straps; and
commanding, by the controller, at least one adjustment actuator to adjust a position of at least one strap of the plurality of straps to achieve a desired fit of the head mounted display on the user based on the monitored strap pressure data, the captured strap pressure data, and the accepted strap position data of each strap of the user fit information.

12. The method of claim 11, wherein the method further comprises:
adjusting the strap position of one or more straps of the plurality of straps using the at least one adjustment actuator to achieve an accepted fit of the head mounted display on the user based on the monitored strap pressure data; and
recording the monitored eye location data, the monitored strap pressure data, and the adjusted strap position data of each strap associated with the accepted eye location data, the accepted strap pressure data, and the accepted strap position data of each strap respectively of the user fit information associated with the user.

13. The method of claim 11, wherein the plurality of straps comprises:
a crown strap including a first end and a second end, the second end of the crown strap coupled to the display device proximate a top center portion of the display device;
a first temple strap including a first end and a second end, the first end of the first temple strap coupled to the display device proximate a first side portion of the display device; and a second temple strap including a first end and a second end, the first end of the second temple strap coupled to the display device proximate a second side portion of the display device opposite the first side portion of the display device, and the second end of the second temple strap coupled to the second end of the crown temple strap and the second end of the first temple strap, wherein the monitored strap pressure data is determined based on pressure sensor data from the plurality of pressure sensors and strap position data for the crown strap, the first temple strap and the second temple strap.

14. The method of claim 11, wherein:

an image being displayed on the display device includes an alignment crosshair and an alignment marker associated with a respective eye of the at least one eye of the user, and wherein a desired image is achieved when the alignment marker is aligned with the alignment crosshair associated with the respective eye.

15. The method of claim 11, wherein the method further comprises:

monitoring strap position data of each respective strap of the plurality of straps using each of a plurality of strap position sensors of the head mounted display, wherein each of the plurality of strap position sensors associated with a respective strap of the plurality of straps, and adjusting the position of a respective strap of the plurality of straps based on the strap position data of the respective strap of the plurality of straps.

16. The method of claim 11, wherein the method further comprises:

monitoring context information associated with the head mounted display;

when the monitored context information indicates that the accepted fit of the head mounted display on the user is to be changed, adjusting the position of each strap of the plurality of straps using the at least one adjustment actuator to achieve an updated fit of the head mounted display based on the monitored strap pressure data and the monitored context information, wherein the updated fit is within an operational range of the head mounted display that is greater than or equal to a loose fit threshold and less than or equal to a tight fit threshold.

17. The method of claim 16, wherein:

the monitored context information indicates that the accepted fit of the head mounted display on the user is to be changed is based on one or more of a motion sensor of the head mounted display detects that movement of the head mounted display has exceeded a high movement change threshold, the motion sensor detects that movement of the head mounted display has decreased below a low movement change threshold, an activity indicator is received that indicates that that movement of the head mounted display is to exceed the high movement change threshold, the motion sensor indicates that movement of the head mounted display is to decrease below the low movement change threshold, and the monitored strap pressure data indicates that the desired fit of the head mounted display on the user has changed such that the desired fit is outside the operational range of the head mounted display.

18. The method of claim 11, wherein the method further comprises:

authenticating the user using an authentication process and one or more authentication devices coupled to the head mounted display, wherein the authentication process comprises one or more of IRIS recognition, facial recognition, finger recognition, retina recognition, voice recognition, username and password verification, and wherein the identification of the user fit information associated with the user of the head mounted display is based on the authentication process.

19. The method of claim 11, wherein:

commanding the at least one adjustment of actuator to adjust the position of at least one strap of the plurality of straps based on at least one of a hand gesture by the user, a head gesture by the user, a voice command by the user, and adjustment input provided by an adjustment input device of the head mounted display initiated by the user.

20. The method of claim 11, wherein the method comprises:

rotating, by a drive stepper motor of the at least one adjustment actuator, a drive pinion of the at least one adjustment actuator in a first rotational direction causing the drive pinion to move in a first direction along a drive rack of the at least one adjustment actuator tightening each strap; and rotating, by the drive stepper motor, the drive pinion in a second rotational direction causing the drive pinion to move in a second direction along the drive rack loosening each strap, and wherein the second rotational direction is opposite the first rotational direction and the second direction is opposite the first direction.

* * * * *